(12) United States Patent
Frieder et al.

(10) Patent No.: US 11,410,763 B2
(45) Date of Patent: *Aug. 9, 2022

(54) METHOD AND SYSTEM FOR ASSESSING DRUG EFFICACY USING MULTIPLE GRAPH KERNEL FUSION

(71) Applicant: Georgetown University, Washington, DC (US)

(72) Inventors: Ophir Frieder, Chevy Chase, MD (US); Hao-Ren Yao, McLean, VA (US); Der-Chen Chang, Burtonsville, MD (US)

(73) Assignee: Georgetown University, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/555,675

(22) Filed: Dec. 20, 2021

(65) Prior Publication Data

US 2022/0115104 A1 Apr. 14, 2022

Related U.S. Application Data

(63) Continuation of application No. 17/088,172, filed on Nov. 3, 2020, now Pat. No. 11,238,966.

(Continued)

(51) Int. Cl.
*G16H 20/10* (2018.01)
*G16H 70/40* (2018.01)
(Continued)

(52) U.S. Cl.
CPC ............ *G16H 20/10* (2018.01); *G06F 9/545* (2013.01); *G06K 9/6267* (2013.01); *G06N 7/005* (2013.01); *G16H 50/80* (2018.01); *G16H 70/40* (2018.01)

(58) Field of Classification Search
CPC ........ G16H 20/10; G16H 50/80; G16H 70/40; G06F 9/545; G06K 9/6267; G06N 7/005
(Continued)

(56) References Cited

U.S. PATENT DOCUMENTS

2014/0095201 A1* 4/2014 Farooq ................... G16H 50/30
705/3
2019/0053726 A1* 2/2019 Geva ....................... G16Z 99/00
(Continued)

OTHER PUBLICATIONS

Yao, H., et al., "Multiple Graph Kernel Fusion Prediction of Drug Prescription," Sep. 2019, 10th ACM International Conference; 10 pages.

(Continued)

*Primary Examiner* — Jason S Tiedeman
*Assistant Examiner* — Rachel F Durnin
(74) *Attorney, Agent, or Firm* — Smith Gambrell & Russell LLP

(57) ABSTRACT

Embodiments of the present systems and methods may provide techniques to predict the success or failure of a drug used for disease treatment. For example, a method of determining drug efficacy may include, for a plurality of patients, generating a directed acyclic graph from health related information of each patient comprising nodes representing a medical event of the patient, at least one first edge connecting the first node to an additional node, each additional edge connecting nodes representing two consecutive medical events, the edge having a weight based on a time difference between the two consecutive medical events, capturing a plurality of features from each directed acyclic graph, generating a binary graph classification model on captured features of each directed acyclic graph, determining a probability that a drug or treatment will be effective using the binary graph classification model, and determining a drug to be prescribed to a patient based on the determined probability.

30 Claims, 20 Drawing Sheets

Related U.S. Application Data

(60) Provisional application No. 63/042,676, filed on Jun. 23, 2020, provisional application No. 62/930,072, filed on Nov. 4, 2019.

(51) Int. Cl.
  *G06F 9/54* (2006.01)
  *G06N 7/00* (2006.01)
  *G06K 9/62* (2022.01)
  *G16H 50/80* (2018.01)

(58) Field of Classification Search
  USPC .............................................. 705/2–3; 600/3
  See application file for complete search history.

(56) References Cited

U.S. PATENT DOCUMENTS

2019/0130069 A1*  5/2019  Li .......................... G16H 20/00
2020/0176113 A1*  6/2020  Megerian ............... G16H 50/70

OTHER PUBLICATIONS

Yao, H., et al., "Graph Kernel Prediction of Drug Prescription," May 2019, IEEE EMBS International Conference on Biomedial & Health Informatics (BHI), 10th ACM International Conference; 4 pages.

* cited by examiner

METHOD AND SYSTEM FOR ASSESSING DRUG EFFICACY USING MULTIPLE GRAPH KERNEL FUSION

CROSS-REFERENCE TO RELATED APPLICATIONS

This patent application is a continuation of U.S. patent application Ser. No. 17/088,172, filed Nov. 3, 2020, which claims the benefit of U.S. Provisional Application No. 62/930,072, filed Nov. 4, 2019 and claims the benefit of U.S. Provisional Application No. 63/042,676, filed Jun. 23, 2020, the contents of all of which are incorporated herein in their entirety.

BACKGROUND

The present invention relates to systems and methods that may provide techniques to predict the success or failure of a drug used for disease treatment using an accurate and efficient model to predict the success potential of a specific drug prescription for a given ailment.

Erroneous medication prescription is defined as a failure in the medication treatment process that results in an unsuccessful treatment or harmful outcome to patients. Clinicians have the responsibility to accurately diagnose and adequately treat a patient's disease. For treatments that require medications, the ideal prescription is the one that is most effective and presents the least harmful side effects. Yet, this is not always achieved. Further, for newly emergent diseases, it is important that effective treatments be identified quickly and efficiently.

For example, at present, there are few, if any, fully approved coronavirus treatments. Remdesivir, a new intravenous antiviral, received an FDA emergency use authorization. However, researchers are testing existing medications (targeted for treatment of other conditions) for COVID-19 treatment. Such drugs being tested may include, for example, Remdesivir, a new drug, Dexamethasone, a corticosteroid currently used for autoimmune and allergic reactions, Hydroxychloroquine and Chloroquine, currently used for malaria & autoimmune diseases, Azithromycin, an antibiotic currently used for bronchitis & pneumonia, Tocilizumab (Actemra), currently used for Rheumatic arthritis, Kaletra (lopinavir/ritonavir), currently used as an HIV medication, Tamiflu currently used for Influenza, Colchicine currently used for Gout, etc. Many such medications are used by thousands or millions of patients for whom medical records are available. Further, COVID-19 treatments are cohort specific, with varying guidelines for identifying patients depending on their health. For example, patients with history of cancer, diabetes, digestive and liver health, etc. have different care guidelines. Accordingly, the likelihood of success of a particular drug may vary with patient history and demographics.

The rapid growth of patient Electronic Health Records (EHRs) provides opportunities to develop a data-driven analytical application on medical data. Many approaches for many medical applications exist.

Due to the complex nature of EHR data, implementing a predictive model is difficult. For example, electronic phenotyping is the process of extracting relevant features from EHRs, a major step before performing an analytical task. Such approaches transform EHRs into vector representations via various feature extraction techniques (e.g., electronic phenotyping). The extracted feature vectors, where each dimension corresponds to a certain medical concept, are fed into a linear classifier. This flattening formulation of EHRs ignores temporal relationships between medical events in a patient's history, reducing effectiveness. On the other hand, many extraction tasks require domain medical knowledge to generate hand-crafted features, which is not efficient and cost prohibitive at large scale. Thus, as a feature extraction technique, electronic phenotyping may cause information loss on the discriminant features.

Recently, the emergence of deep learning models pose other ways to analyze EHR data (e.g., EHR data embedding) which achieve better performance with significantly less feature engineering. However, result interpretation of such systems is difficult. For example, Recurrent Neural Networks (RNN) model time series medical data. However, interpretability concerns associated with deep learning approaches, particularly in the medical domain, limit their use. Notwithstanding, the trade-off to achieve high accuracy and high interpretability remains.

Many studies introduce attention-based RNN models to improve interpretability. However, the majority of efforts rely on publicly available datasets or on a collaborating hospital's EHR system where patient demographic information is mostly uniform. Unfortunately, this uniformity of data fails to exist when developing approaches for real-world, integrated EHR systems (e.g., insurance claim-based EHR systems). On this occasion, highly temporally dependent data attributes with high noise and variance often induce model over-fitting. Such a problem may be addressed with a proposed graph-kernel EHR predictive model, yet they only consider a single medication with immediate outcome observations. For chronic diseases, long-term disease progression coupled with EHR complexity complicates the effort. Thus, attention-based deep learning models and handcrafted kernel computations are limited to handle complex EHR under long-term disease progression. The increased divergence and noise on data attributes over-fit the deep learning model and defeat the handcrafted kernel.

Accordingly, a need arises for techniques to predict the success or failure of a drug used for disease treatment that may provide improved accuracy and efficiency and may provide identification drugs most likely to be effective that are patient-specific as well as disease specific.

SUMMARY

Embodiments of the present systems and methods may provide techniques to predict the success or failure of a drug used for disease treatment using an accurate and efficient model to predict the success potential of a specific drug prescription for a given ailment. For example, embodiments may predict success or failure of drug prescription by formulating a binary graph classification problem without the need of electronic phenotyping. First, training data may be identified, such as success and failure patients for target disease treatment within a user-defined time period. The set of medical events from patient Electronic Health Records (EHRs) that occur within this time quantum may be extracted. Then, a classification task may be performed on the graphical representation of the patient EHRs. The graphical representation provides an opportunity to model the EHRs in a compact structure with high interpretability.

As disclosed herein, patients need not be human. That is, the methods and systems disclosed herein are applicable to any animal, human or non-human, under clinical care. Embodiments disclosed are exemplified without loss of generality using human patients.

Embodiments of the present systems and methods may provide a kernel based deep architecture to predict the success or failure for drug prescription given to a patient. The success and failure of medications on patients may be identified to provide targeted disease treatment. An EHR prior to the disease diagnosis is included for each patient, and their graphical representation (e.g., patient graph), where nodes denote all medical events with day differences as edge weights, are built. The binary graph classification task is performed directly on the patient graph via a deep architecture. Interpretability is readily available and easily accepted by users without further post-processing due to the nature of the graph structure.

Embodiments of the present systems and methods may provide a novel graph kernel, Temporal proximity kernel, which efficiently calculates temporal similarity between two patient graphs. The kernel function is proven to be positive definite, increasing the model availability by using a kernelized classifier such as Support Vector Machine (SVM). To obtain the multi-view aspect, we combine the temporal proximity kernel with the node kernel and the shortest path kernel as a single kernel through multiple kernel learning.

To perform large scale and noise-resistant learning objectives, embodiments may transfer the original task to similarity-based classification, where each row in the kernel gram matrix is considered as a feature vector with each dimension expressing the similarity measurement with specific training examples. A multiple graph kernel fusion approach is proposed to learn kernel representation in an end-to-end manner for the best kernel combination. We argue that representation learning is a typical kernel approximation which preserves the similarity while reducing the dimension for the original kernel matrix. The embedding weight for each kernel supports the interpretation to the prediction via most similar cases by selecting one or a plurality of top relevant embedding dimension(s).

Embodiments of the present systems and methods may provide a cross-global attention graph kernel network to learn optimal graph kernels on a graphical representation of patient EHRs. The novel cross-global attention node matching automatically captures relevant information in biased long-term disease progression. In contrast to attention-based graph similarity learning that relies on a pairwise comparisons of training pairs or triplets, our matching is performed on a batch of graphs simultaneously by a global cluster membership assignment. This is accomplished without the need to generate training pairs or triplets for pairwise computations and seamlessly combines classification loss. The learning process is guided by cosine distance. The resulting kernel, compared to its Euclidean distance counterpart, has better noise resistance under a high dimension space. Unlike distance metric learning and aforementioned graph similarity learning, we align our learned distance and graph kernel to a classification objective. We formulate an end-to-end training by jointly optimizing contrastive and kernel alignment loss with a Support Vector Machine (SVM) primal objective. Such a training procedure encourages node matching and similarity measurement to produce ideal classification, providing interpretation on prediction. The resulting kernel function can be directly used by an off-the-shelf kernelized classifier (e.g., scikit-learn SVC). The cross-global attention node matching and kernel-based classification makes it interpretable in both knowledge discovery and prediction case study.

Embodiments may provide one-shot disease processing, for example, for an antibiotic medication. To perform one-shot disease processing, a database of medical history data may be partitioned according to disease diagnosis. A suggested medication may be attached to the data and used to predict a likelihood of success or failure of the medication and to identify similar individuals.

Embodiments may provide COVID-19 processing based on a presumptive medication. A database of medical history data may be partitioned according to those having used the presumptive medication. Patient graphs may be retained up until the last presumptive medication use within a surveillance window. A suggested medication may be attached to the data and used to identify similar individuals indicating a likelihood of success or failure of use of the suggested medication for others diseases under consideration.

For example, in an embodiment, a method of determining drug efficacy may be implemented in a computer system comprising a processor, memory accessible by the processor and storing computer program instructions an data, and computer program instructions to perform for a plurality of patients, generating a directed acyclic graph from health related information of each patient, each directed acyclic graph comprising a first node representing first demographic information of the patient, a plurality of additional nodes, each additional node representing a medical event of the patient, at least one first edge connecting the first node to an additional node, the first edge having a weight based on second demographic information of the patient, and a plurality of additional edges, each additional edge connecting nodes representing two consecutive medical events, the edge having a weight based on a time difference between the two consecutive medical events, capturing a plurality of features from each directed acyclic graph, generating a binary graph classification model on captured plurality of features of each directed acyclic graph, determining a probability that a drug or treatment will be effective using the binary graph classification model, and determining a drug to be prescribed to a patient based on the determined probability.

In embodiments, the plurality of features may be captured by transforming each directed acyclic graph to a shortest path graph, generating a temporal topological kernel by recursively calculating similarity among temporal ordering on a plurality of groups of additional nodes, and generating a temporal substructure kernel on additional edges connecting additional nodes in each group of additional nodes. The plurality of features may be captured by generating a topological ordering of each directed acyclic graph based on an order of occurrence of a label associated with each additional node in each directed acyclic graph, generating a topological sequence of each directed acyclic graph comprising a plurality of levels indicating an order of occurrence of a same node label in the topological sequence, generating a temporal signature for each directed acyclic graph comprising a series of total passage times from the first node to each additional node in a union of a plurality of topological sequences, generating a temporal proximity kernel between a plurality of pairs of temporal signatures, generating a shortest path kernel by calculating an edge walk similarity on shortest path graphs for a plurality of pairs of directed acyclic graphs, generating a node kernel by comparing node labels of a plurality of pairs of directed acyclic graphs, and fusing the temporal proximity kernel, the shortest path kernel, and the node kernel. The fusing may comprise reducing dimensions of the temporal proximity kernel, the shortest path kernel, and the node kernel for the plurality of pairs of directed acyclic graphs, and averaging embeddings of the temporal proximity kernel, the shortest path kernel, and the node kernel for the plurality of pairs of directed acyclic graphs. Determining a success or failure of the fusion may comprise using a sigmoid layer.

In an embodiment, a system for determining drug efficacy may comprise a processor, memory accessible by the processor, and computer program instructions stored in the memory and executable by the processor to perform for a plurality of patients, generating a directed acyclic graph from health related information of each patient, each directed acyclic graph comprising a first node representing first demographic information of the patient, a plurality of additional nodes, each additional node representing a medical event of the patient, at least one first edge connecting the first node to an additional node, the first edge having a weight based on second demographic information of the patient, and a plurality of additional edges, each additional edge connecting nodes representing two consecutive medical events, the edge having a weight based on a time difference between the two consecutive medical events, capturing a plurality of features from each directed acyclic graph, generating a binary graph classification model on captured plurality of features of each directed acyclic graph, determining a probability that a drug or treatment will be effective using the binary graph classification model, and determining a drug to be prescribed to a patient based on the determined probability.

In an embodiment, a computer program product for determining drug efficacy may comprise a non-transitory computer readable storage having program instructions embodied therewith, the program instructions executable by a computer, to cause the computer to perform a method that may comprise for a plurality of patients, generating a directed acyclic graph from health related information of each patient, each directed acyclic graph comprising a first node representing first demographic information of the patient, a plurality of additional nodes, each additional node representing a medical event of the patient, at least one first edge connecting the first node to an additional node, the first edge having a weight based on second demographic information of the patient, and a plurality of additional edges, each additional edge connecting nodes representing two consecutive medical events, the edge having a weight based on a time difference between the two consecutive medical events, capturing a plurality of features from each directed acyclic graph, generating a binary graph classification model on captured plurality of features of each directed acyclic graph, determining a probability that a drug or treatment will be effective using the binary graph classification model, and determining a drug to be prescribed to a patient based on the determined probability.

BRIEF DESCRIPTION OF THE DRAWINGS

The details of the present invention, both as to its structure and operation, can best be understood by referring to the accompanying drawings, in which like reference numbers and designations refer to like elements.

DETAILED DESCRIPTION

Figure 1:
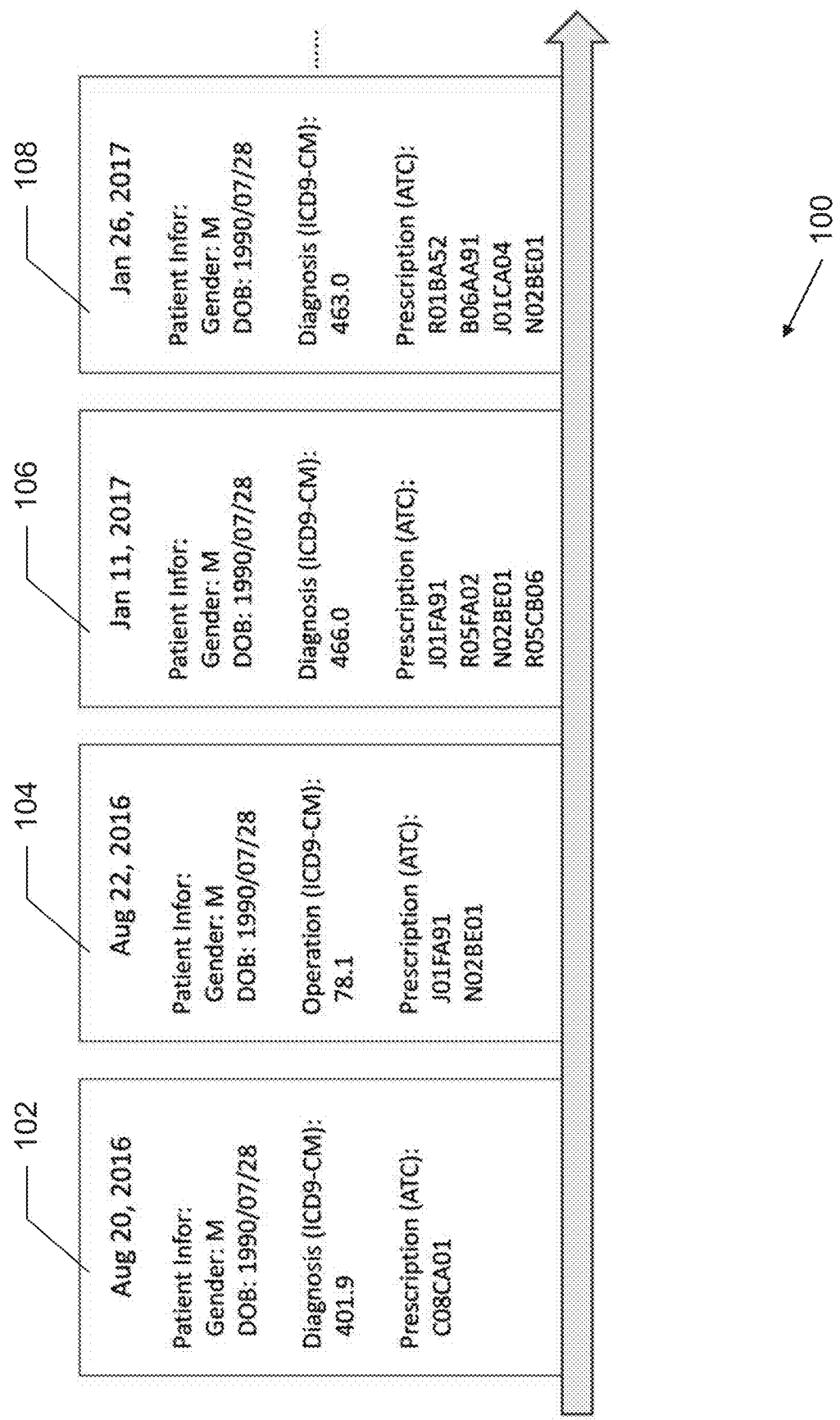
FIG. 1 is an exemplary illustration of set of patient EHRs, according to embodiments of the present systems and methods.

Embodiments of the present systems and methods may provide techniques to predict the success or failure of a drug used for disease treatment using an accurate and efficient model to predict the success potential of a specific drug prescription for a given ailment. For example, embodiments may predict success or failure of drug prescription by formulating a binary graph classification problem without the need of electronic phenotyping. First, training data may be identified, such as success and failure patients for target disease treatment within a user-defined time period. The set of medical events from patient Electronic Health Records (EHRs) that occur within this time quantum may be extracted. Then, a classification task may be performed on the graphical representation of the patient EHRs. The graphical representation provides an opportunity to model the EHRs in a compact structure with high interpretability.

Embodiments of the present systems and methods may provide a kernel based deep architecture to predict the success or failure for drug prescription given to a patient. The success and failure of medication on patients are identified for targeted disease treatment to generate are used to define the success and failure cases. An EHR prior to the disease diagnosis is included for each patient, and their graphical representation (e.g., patient graph), where nodes denote all medical events with day differences as edge weights, are built. The binary graph classification task is performed directly on the patient graph via a deep architecture. Interpretability is readily available and easily accepted by users without further post-processing due to the nature of the graph structure.

Embodiments of the present systems and methods may provide a novel graph kernel, Temporal proximity kernel, which efficiently calculates temporal similarity between two patient graphs. The kernel function is proven to be positive definite, increasing the model availability by using a kernelized classifier such as Support Vector Machine (SVM). To obtain the multi-view aspect, we combine the temporal proximity kernel with the node kernel and the shortest path kernel as a single kernel through multiple kernel learning.

To perform large scale and noise-resistant learning objectives, embodiments may transfer the original task to similarity-based classification, where each row in the kernel gram matrix is considered as a feature vector with each dimension expressing the similarity measurement with specific training examples. A multiple graph kernel fusion approach is proposed to learn kernel representation in an end-to-end manner for the best kernel combination. We argue that representation learning is a typical kernel approximation which preserves the similarity while reducing the dimension for the original kernel matrix. The embedding weight for each kernel supports the interpretation to the prediction via most similar cases by selecting top relevant embedding dimension.

Embodiments of the present systems and methods may provide a cross-global attention graph kernel network to learn optimal graph kernels on a graphical representation of patient EHRs. The novel cross-global attention node matching automatically captures relevant information in biased long-term disease progression. In contrast to attention-based graph similarity learning that relies on a pairwise comparisons of training pairs or triplets, our matching is performed on a batch of graphs simultaneously by a global cluster membership assignment. This is accomplished without the need to generate training pairs or triplets for pairwise computations and seamlessly combines classification loss. The learning process is guided by cosine distance. The resulting kernel, compared to its Euclidean distance counterpart, has better noise resistance under a high dimension space. Unlike distance metric learning and aforementioned graph similarity learning, we align our learned distance and graph kernel to a classification objective. An end-to-end training may be formulated by jointly optimizing contrastive and kernel alignment loss with a Support Vector Machine (SVM) primal objective. Such a training procedure encourages node matching and similarity measurement to produce ideal classification, providing interpretation on prediction. The resulting kernel function can be directly used by an off-the-shelf kernelized classifier (e.g., scikit-learn SVC). The cross-global attention node matching and kernel-based classification makes it interpretable in both knowledge discovery and prediction case study.

In embodiments, up to three kernels may be used to achieve multi-view similarity measurement—reducing potential medical record "noise". For example, some training examples may dominate prediction results due to higher kernel value. Embodiments may incorporate additional kernels to balance this effect to improve prediction. Example of kernels that may be used include a Temporal Proximity Kernel, which may provide temporal ordering and time difference of medical events, a Shortest Path Kernel, which may provide general connectivity of medical events, and a Node Kernel, which may provide general overlapping of medical events.

Embodiments may provide one-shot disease processing, for example, for an antibiotic medication. To perform one-shot disease processing, a database of medical history data may be partitioned according to disease diagnosis. A suggested medication may be attached to the data and used to predict a likelihood of success or failure of the medication and to identify similar individuals.

Embodiments may provide COVID-19 processing based on a presumptive medication. A database of medical history data may be partitioned according to those having used the presumptive medication. Patient graphs may be retained up until the last presumptive medication use within a surveillance window. A suggested medication may be attached to the data and used to identify similar individuals indicating a likelihood of success or failure of use of the suggested medication for others diseases under consideration.

An exemplary set of patient EHRs 100 is shown in FIG. 1. EHRs 100 may include a plurality of records 102-108. Typically, each record relates to a different patient interaction with medical staff, diagnosis, test result, etc., and may include information such as the date of the interaction, diagnosis, test result, etc., demographic information about the patient, such as identity, gender, date of birth, etc., information about the diagnosis or diagnoses, information about the prescription(s), etc.

Figure 2:
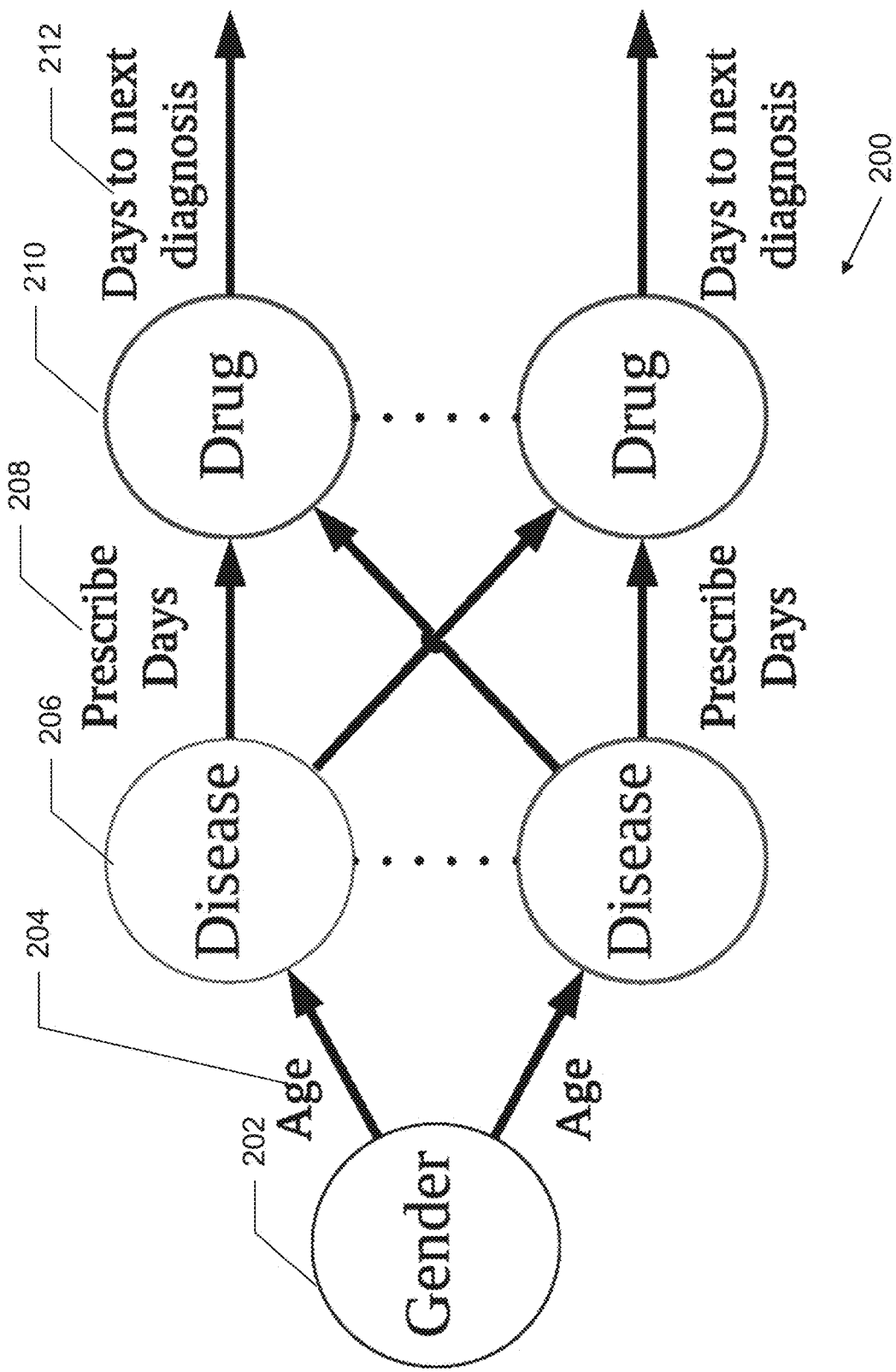
FIG. 2 is an exemplary illustration of a Directed Acyclic Graph (DAG), according to embodiments of the present systems and methods.

A patient's EHR may be formulated as a Directed Acyclic Graph (DAG) 200, an example of which is shown in FIG. 2. For example, each node represents a medical event, such as a disease diagnosis 206, a drug prescription 210, etc., and an edge between two nodes represents an ordering with the time difference as edge weight (e.g., days). For example, the edge weights may include the prescription day 208, the days to next diagnosis 212, etc. The demographic information of the patient, such as, gender, may be represented as a node 202 that connects to the first medical event 206 with age 204 as an edge weight. In this example, only gender and age are used as demographic information to simplify the model.

Figure 13:
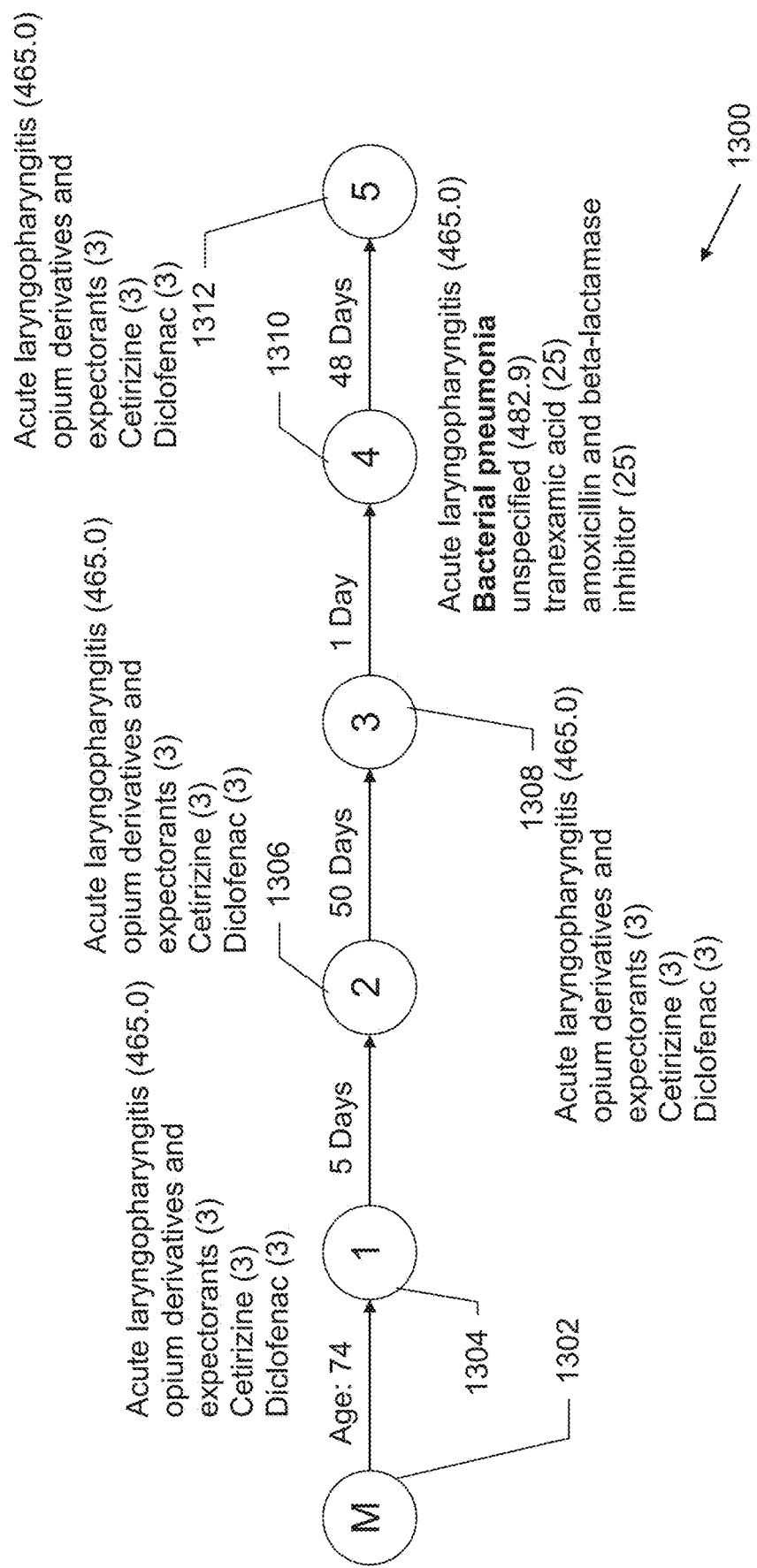
FIG. 13 is an exemplary illustration of a patient DAG illustrating success with pneumonia treatment, according to embodiments of the present systems and methods.

A more detailed example 1300 of a patient DAG illustrating success with pneumonia treatment is shown in FIG. 13. In this example, the diagnosis at each stage 1304-1312 of treatment, as well as the prescriptions at each stage of treatment are shown. This example illustrates a success because there is no diagnosis of pneumonia for more than four weeks after the end of the course of treatment, stage 5 1312.

Figure 14:
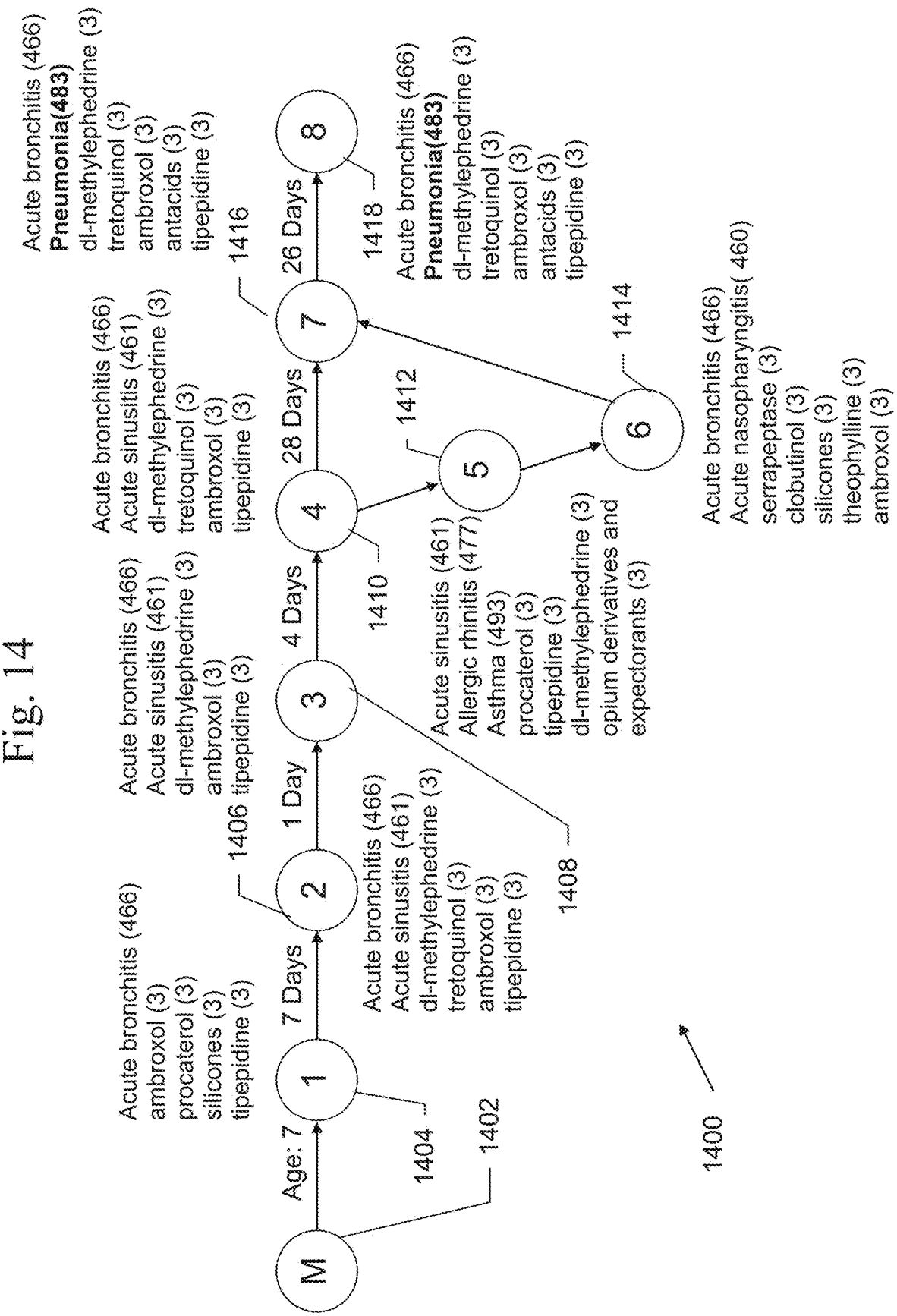
FIG. 14 is an exemplary illustration of a patient DAG illustrating failure with pneumonia treatment, according to embodiments of the present systems and methods.

A more detailed example 1400 of a patient DAG illustrating failure with pneumonia treatment is shown in FIG. 14. In this example, the diagnosis at each stage 1404-1418 of treatment, as well as the prescriptions at each stage of treatment are shown. This example illustrates a failure in treatment of pneumonia 1416 because there is a diagnosis of pneumonia within four weeks after a stage of treatment at stage 8 1418.

In embodiments, an EHR graph representation may be defined as follows: Given n medical events, set $M=\{(m_1, t_1), \ldots, (m_n, t_1)\}$ represents a patient's EHR with $m_i$ denoting a medical event such as diagnosis, and $t_i$ denoting the time for $m_i$. Then the patient graph may be defined as follows: Definition 1 (Patient Graph). The patient graph $P_g=(V,E)$ of events M is a weighted directed acyclic graph with its vertices V containing all events $m_i \in M$ and edges E containing all pairs of consecutive events $(m_i, m_j)$. The edge weight from node i to node j is defined as $W_{ij}=t_j-t_i$, which defines the time interval between $m_i$, $m_j$.

Figure 3:
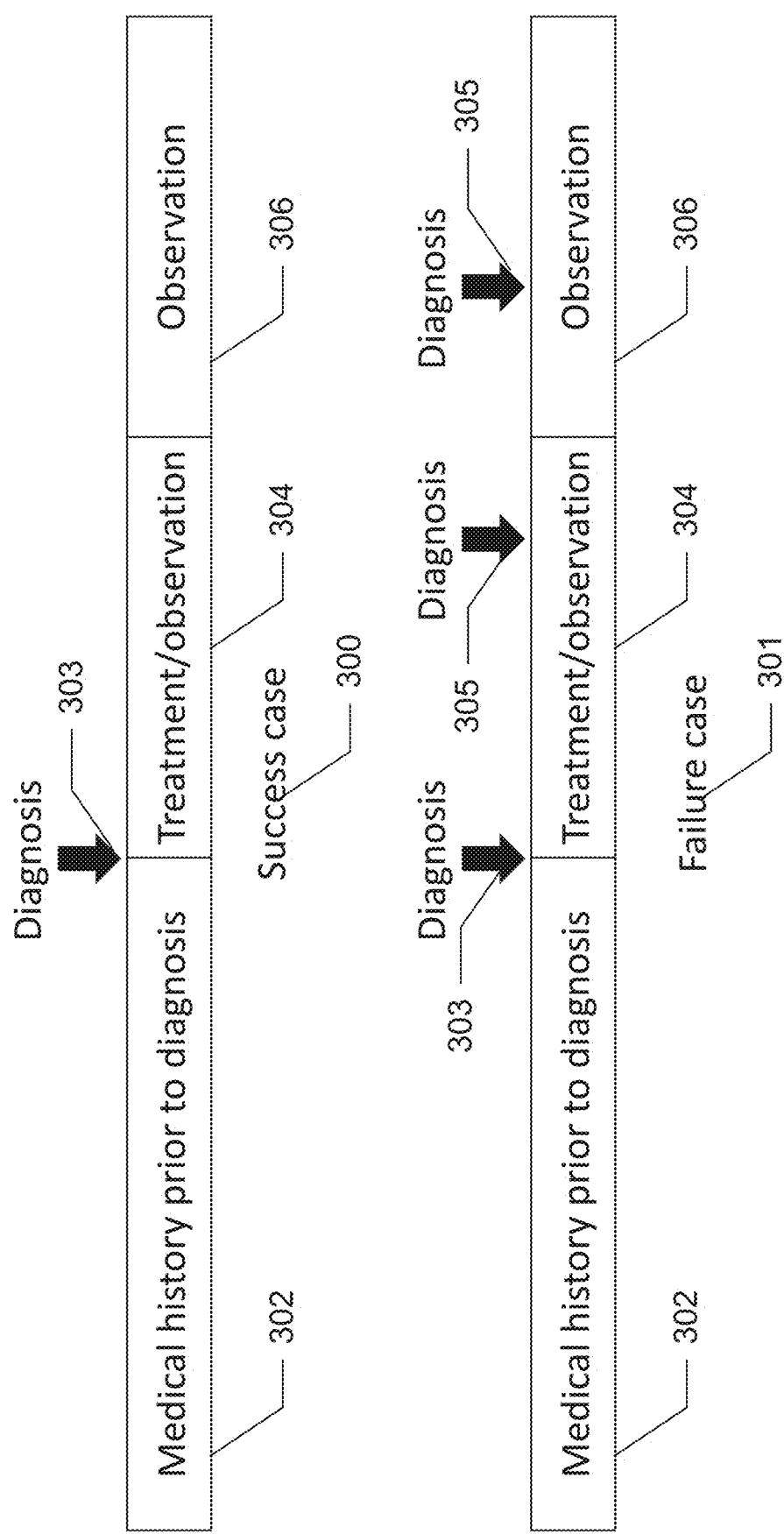
FIG. 3 is an exemplary illustration of examples of success and failure cases, according to embodiments of the present systems and methods.

Given a disease diagnosis of a patient, a drug prescription for the diagnosis is considered a failure if the patient has a second same diagnosis within an observation window. Otherwise, the prescription is considered a success. Examples of success 300 and failure 301 cases are shown in FIG. 3. The failure case 301 may be labelled as positive, and the success 300 case may be labelled as negative. To capture historical factors, each case may contain previous medical history events 302 prior to the diagnosis date 303 in a user-defined period. Each case may be treated as a subset of patient EHRs as shown in FIG. 1, which contains a multiple-event single-patient EHR. In short, each case contains the medical events before and after the disease diagnosis for a user-defined period. A drug prescription for the diagnosis is considered a failure if the patient has a second same diagnosis 305 within an observation window, which may include a period of treatment and observation 304, and a period of observation 306.

In embodiments, this may be extended to define the success or failure of treatment plan for a chronic disease, following the guidelines published by the National Medical Association for selected chronic diseases. Generally, an observation window 306 is defined after a treatment period 304 (which may include observation as well) to monitor whether the given treatment plan achieves its treatment objective (such as no severe complication occurrence in 5 years). Given a chronic disease diagnosis, a treatment may be considered a failure if the patient is diagnosed 305 with a selected severe complication or comorbidity within the post treatment observation window 306. Otherwise, the treatment may be considered a success. Due to the chronic disease long-term progression where past factors are potentially decisive, all medical histories may be included prior to the first diagnosis date. Each case may be treated as a set of medical records from a patient's EHR as in FIG. 1. The terms patient and case may be used interchangeably herein.

Given a patient EHR, the patient's current diagnosis, and the drug prescription to the current diagnosis, embodiments may predict the success or failure of a prescribed medication. A temporal graph $G_i$ may be created that consists of the current diagnosis, the drug prescription to the current diagnosis, and the medical events in the patient EHR prior to the current diagnosis. Then a binary graph classification problem may be formulated on the resulting temporal graph by considering the following dual optimization problem for a Support Vector Machine (SVM):

$$\underset{\alpha}{\text{maximize}} \sum_i \alpha_i - \frac{1}{2} \sum_{j,k} \alpha_i \alpha_k y_i y_k K(G_j, G_k) \quad (1a)$$

$$\text{subject to } 0 \leq \alpha_i \leq C, i = 1, \ldots, N \quad (1b)$$

$$\sum_i \alpha_i y_i = 0, i = 1, \ldots, N \quad (1c)$$

where K is a positive definite graph kernel on input graphs $G_j$, $G_k$. C is a regularization parameter, and b is a bias term. Given the graph $G_i$, the bias term b can be computed by $$b = y_i - \sum_{j=1} \alpha_j y_j K(G_i, G_j) \quad (2)$$

and the decision function is defined as:

$$f(G) = \sum_{i=1}^{N} \alpha_i y_i K(G_i, G) + b \quad (3)$$

Embodiments may perform a binary graph classification on graph EHR. Given success and failure cases with their associated label $(g_i, y_i)$, we want to learn a classifier such that $f(g_i)=y_i$ where $y_i \in \{0, 1\}$ to predict the success or failure outcome $y_i$ of the given prescription in $g_i$. Embodiments may handle this problem via a kernelized support vector machine (Kernel-SVM) with a graph kernel as described below.

Figure 4:
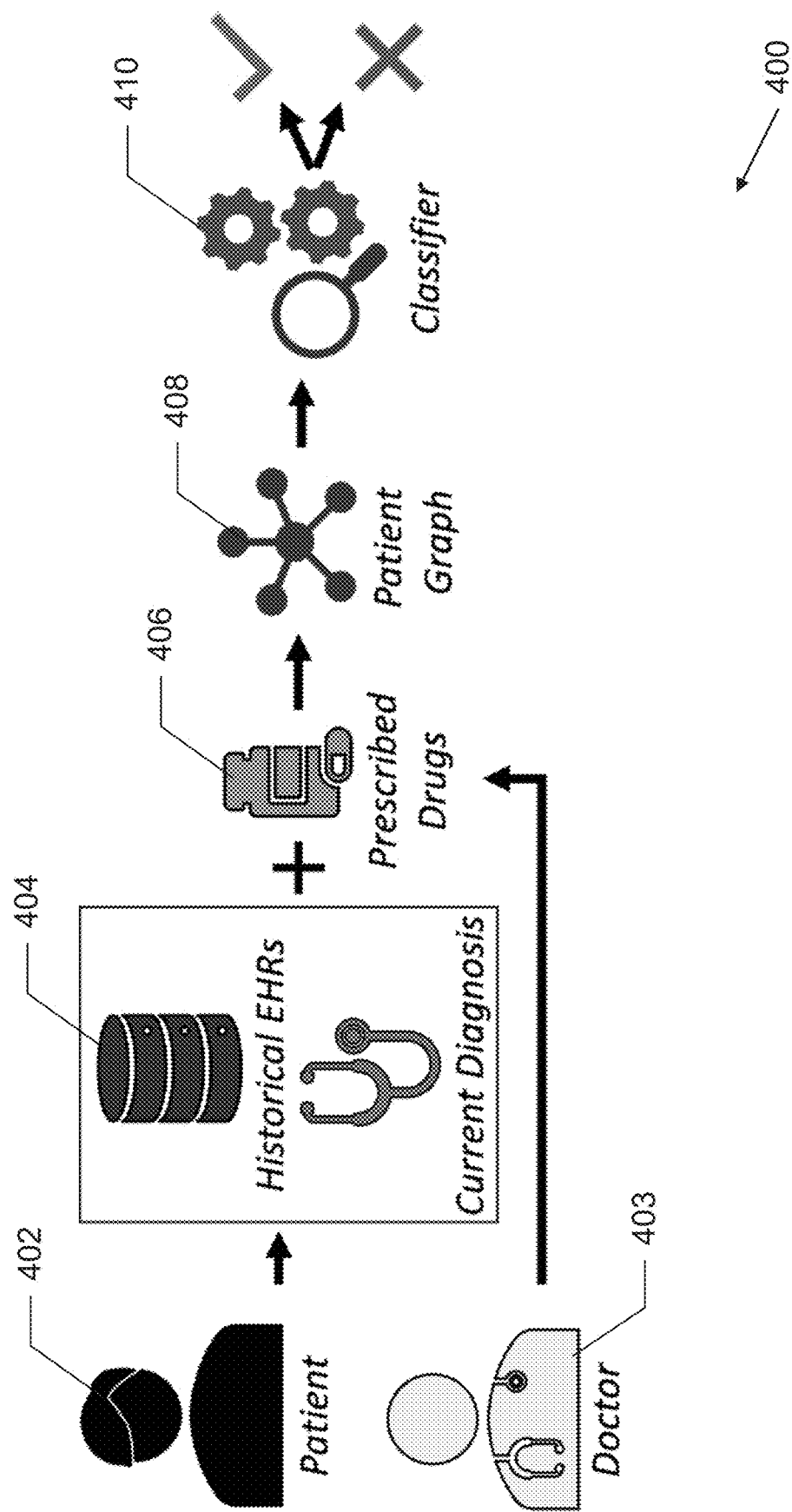
FIG. 4 is an exemplary illustration of a predictive framework directed to predicting effectiveness of a prescribed drug, according to embodiments of the present systems and methods.

An exemplary embodiment of a predictive framework 400 directed to predicting effectiveness of a prescribed drug is shown in FIG. 4. Predictive framework 400 may include information relating to a patient 402, such as historical EHRs, information from a doctor 403, the current diagnosis 404 and the prescribed drug 406, which may be used to generate a patient graph 408, as described above, and then to generate a classifier model 410, which may be used to predict effectiveness of the prescribed drug.

In embodiments, an EHR-based graph kernel may include a Temporal Topological Kernel. To provide an effective treatment, considering the temporal relationships between medical events may be necessary. Embodiments may utilize a temporal topological kernel $K_{tp}$. Specifically, input graphs may be transformed to shortest path graphs and define the kernel function as follows:

Definition 2 (Temporal topological kernel). Let $g_1=(V_1, E_1)$ and $g_2=(V_2,E_2)$ denote the shortest path graph of $P_{g1}$ and $P_{g2}$ by using the transformation discussed above, we define Temporal topological kernel $K_{tp}$ as:

$$K_{tp}(g_1, g_2) = \sum_{e_1 \in E_1, e_2 \in E_2} K_{ts}(e_1, e_2) \quad (4)$$

where $K_{ts}$ is a temporal substructure kernel defined on edges $e_1=(u_1, v_1)$ and $e_2=(u_2, v_2)$ which calculates temporal similarity on substructures that connect to nodes in $e_1$, $e_2$.

The intuition of $K_{tp}$ is based on calculating the similarity among temporal ordering on substructures (e.g., node neighborhoods) by $K_{ts}$ between input graphs, recursively. If two graphs are similar, their temporal order for node neighborhood structures are similar. That is, for a given pair of nodes $v_1$, $v_2$ from two similar graphs $g_1$, $g_2$, the time difference from other nodes $u_i$, $u_j$ in $g_1$, $g_2$ to $v_1$, $v_2$ where $u_i$, $u_j$ lie in the subtrees that connect to $v_1$, $v_2$ must be similar.

Definition 3 (Temporal substructure kernel). Given a pair of edge $e_1=(u_1, v_1)$, $e_2=(u_2, v_2)$, their associated edge weight function $w_1$, $w_2$ of $g_1$, $g_2$, and set of neighbor nodes $N_1, N_2$ of $u_1$, $u_2$, we define temporal substructure kernel $K_{ts}$ as:

$$K_{ts}(e_1, e_2) = \sum_{\substack{e_i = (n_i, u_i) \in E_1, n_i \in N_1 \\ e_j = (n_j, u_2) \in E_2, n_j \in N_2}} K_{ts}(e_i, e_j) \quad (5)$$

$$K_{time}(w_1(e_1), w_2(e_2)) \times K_{node}(u_1, u_2) \times K_{node}(v_1, v_2)$$

and base case definition for the recursion part in Equation 5 when $u_1$ or $u_2$ is the root node:

$$K_{ts}(e_1, e_2) = K_{time}(w_1(e_1), w_2(e_2)) \times K_{node}(u_1, u_2) \times K_{node}(v_1, v_2), \quad (6)$$

where $K_{time}$ is defined as:

$$K_{time}(w_1(e_1), w_2(e_2)) = e^{-1 \times |w_1(e_1) - w_2(e_2)|}, \quad (7)$$

and $K_{node}$ is defined as:

$$K_{node}(u_1, u_2) = \begin{cases} 1, & \text{if label}(u_1) = \text{label}(u_2) \\ 0, & \text{otherwise} \end{cases} \quad (8)$$

To show $K_{ts}$ is a valid kernel, it must be shown that it is positive definite.

Proof $K_{node}$ is a Dirac delta function which is proven to be positive definite. $K_{time}$ is positive definite since the transformation of an exponential function is positive definite. It is known that positive definiteness is closed under positive scalar linear combination and multiplication on positive definite kernels, and it holds in the base case definition in Equation 6. As a result, $K_{ts}$ is positive definite, and $K_{tp}$ is therefore positive definite.

Figure 5:
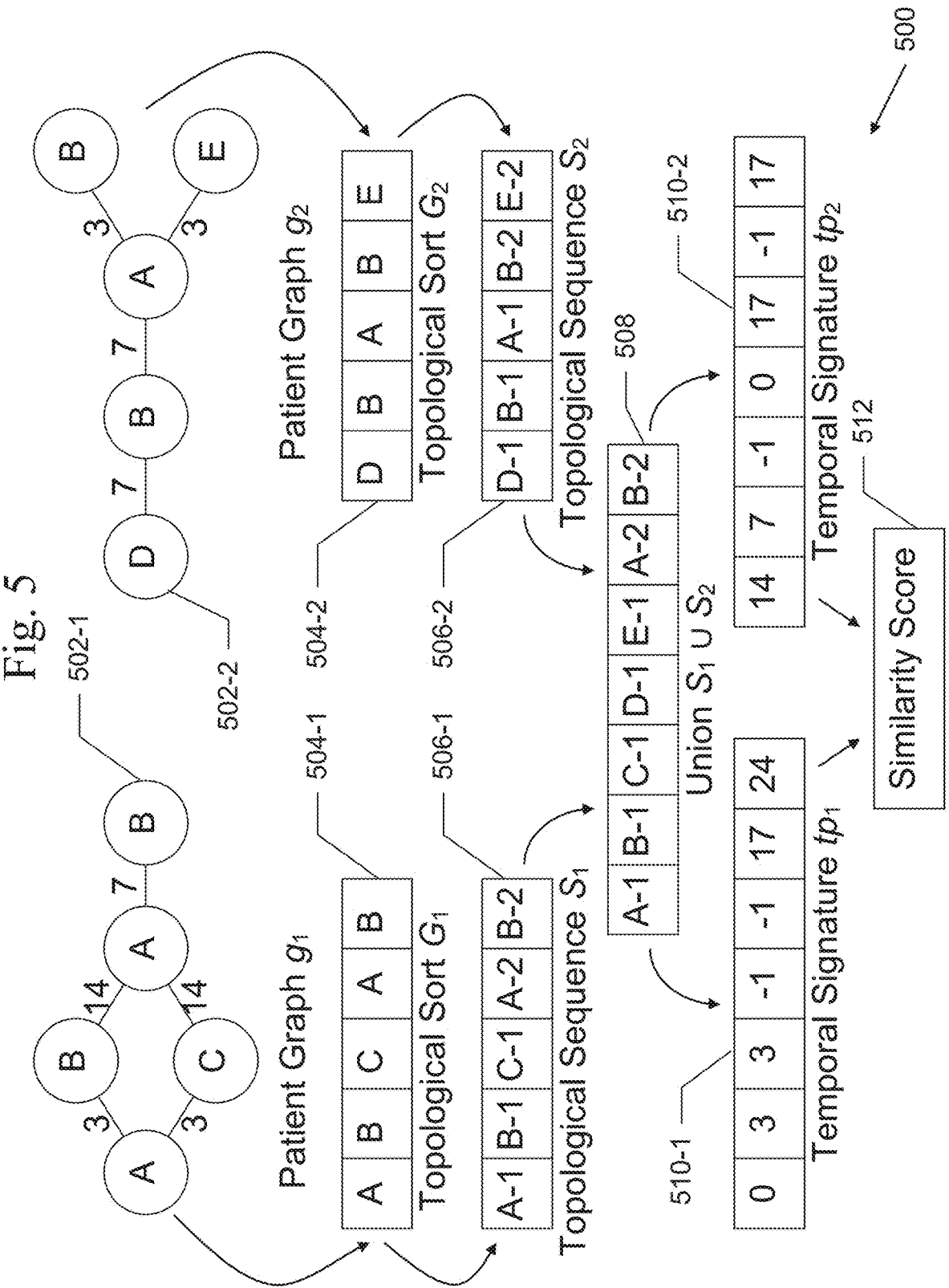
FIG. 5 is an exemplary flow diagram of a process of transferring the input from patient graphs to temporal signatures, according to embodiments of the present systems and methods.

Embodiments may, for a given pair of graph input $g_1, g_2$, calculate their kernel value via a kernel function. In embodiments, an EHR-based graph kernel may include a Temporal proximity kernel, which requires definition of a Topological sequence and a and Temporal signature. An exemplary flow diagram of a process 500 of transferring the input from patient graphs to temporal signatures is shown in FIG. 5. As shown in FIG. 5, process 500 begins with patient graphs $g_1$ 502-1, $g_2$ 502-2. At 504-1, 504-2, a topological sort is performed on each patient graph $g_1$ 502-1, $g_2$ 502-2 to form topological sequences 506-1, 506-2.

To define a topological sequence 506-1, 506-2, let T be a topological ordering of graph $G=(V,E)$ such that $T=\{n_i | i=1, \ldots, |V|\}$, the topological sequence S is defined as $$S = \{n_i \cdot \text{label} + \text{level} | i = 1, \ldots, |V|, \text{ and } n_i \in T\} \quad (9)$$

where + represents the string concatenation and level denotes the order of occurrence of label associated to node $n_i$ in T. Namely, every node in the topological sequence has an attached number to indicate the level. The level indicates the order of occurrence of the same node label in the topological ordering.

At 508, unions of topological sequences 506-1, 506-2 are performed to generate temporal signatures 510-1, 510-2. To define a topological signature, let $S_1$, $S_2$ be topological sequences of two input graphs $g_1$, $g_2$, and $S=S_1 \cup S_2$ with the union set length $m=|S|$. Define the temporal signature for $g_1$ as $tp_1 = \{v_{11}, \ldots, v_{1m}\}$ where $$v_{1j} = \begin{cases} d_j, & \text{if } S[j] \in S_1 \\ -1, & \text{otherwise} \end{cases}, \text{ for } j = 1, \ldots, m \quad (10)$$

and define the temporal signature for $g_2$ as $tp_2 = \{v_{21}, \ldots, v_{2m}\}$ where $$v_{2j} = \begin{cases} d_j, & \text{if } S[j] \in S_2 \\ -1, & \text{otherwise} \end{cases}, \text{ for } j = 1, \ldots, m \quad (11)$$

for $d_j$ denotes the total passage day from the root node to node $n_j$ in its belonging patient graph. Thus, $g_1$ 502-1, $g_2$ 502-2 have been transferred into their vector representations $tp_1$ 510-1, $tp_2$ 510-2.

At 512, a similarity score may be computed. For example, a temporal proximity kernel $K_{tp}$ may calculate the kernel value between $g_1$, $g_2$ via temporal signature $tp_1$, $tp_2$ as:

$$K_{tp}(g_1, g_2) = e^{-\|tp_1 - tp_2\|} \quad (12)$$

where $\|tp_1 - tp_2\|$ is the Euclidean distance between $tp_1$, $tp_2$.

Figure 6:
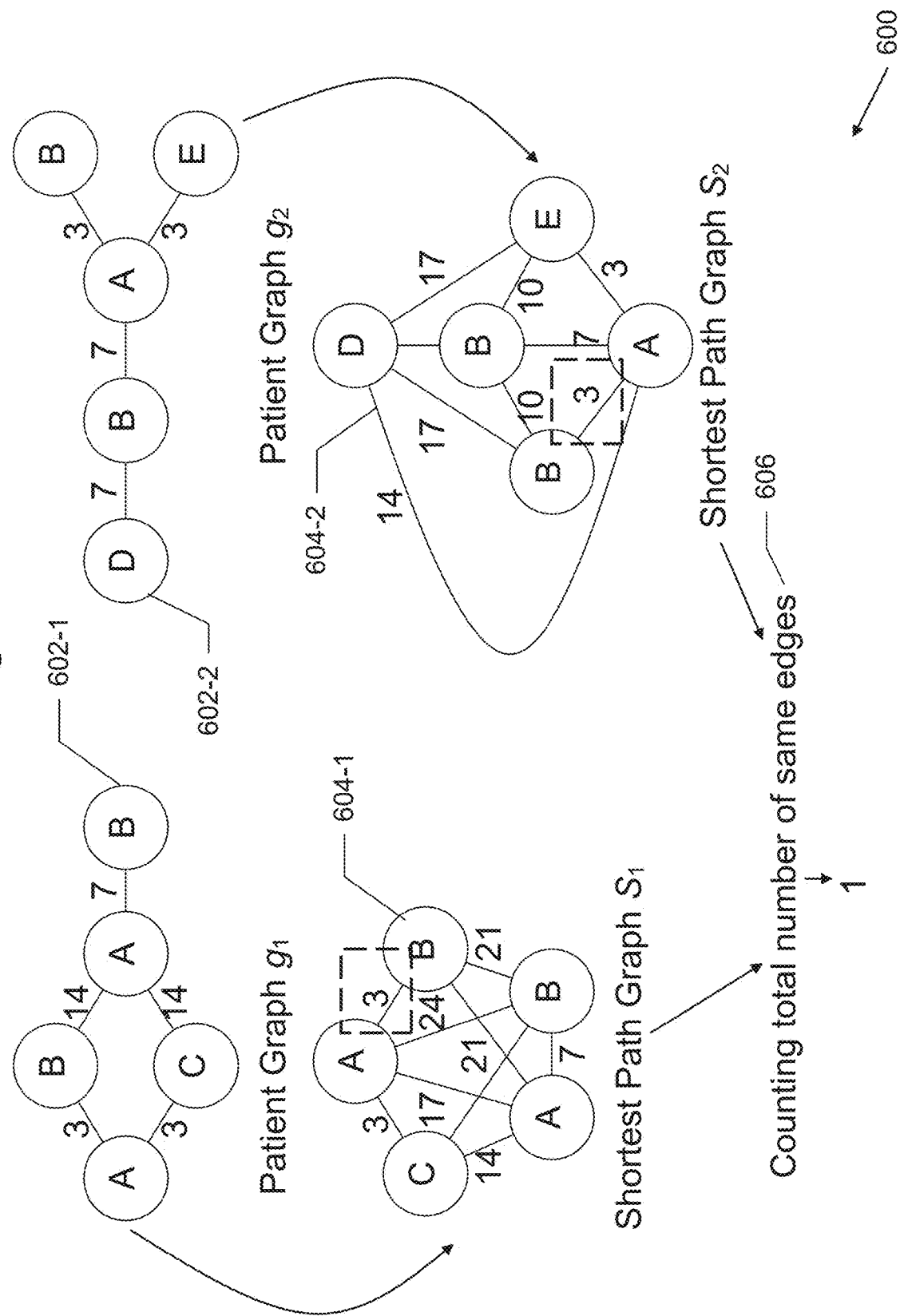
FIG. 6 is an exemplary flow diagram of a process of transferring the input from patient graphs to a shortest path kernel, according to embodiments of the present systems and methods.

An exemplary flow diagram of a process 600 of transferring the input from patient graphs to a shortest path kernel is shown in FIG. 6. As shown in FIG. 6, process 600 begins with patient graphs $g_1$ 602-1, $g_2$ 602-2. At 604-1, 604-2, a shortest path graphs are generated from each patient graph $g_1$ 602-1, $g_2$ 602-2. At 606, a shortest path kernel $K_{sp}$ calculates the edge walk similarity on the shortest path graphs for two input graphs, for example by counting the total number of edges that are the same.

Figure 7:
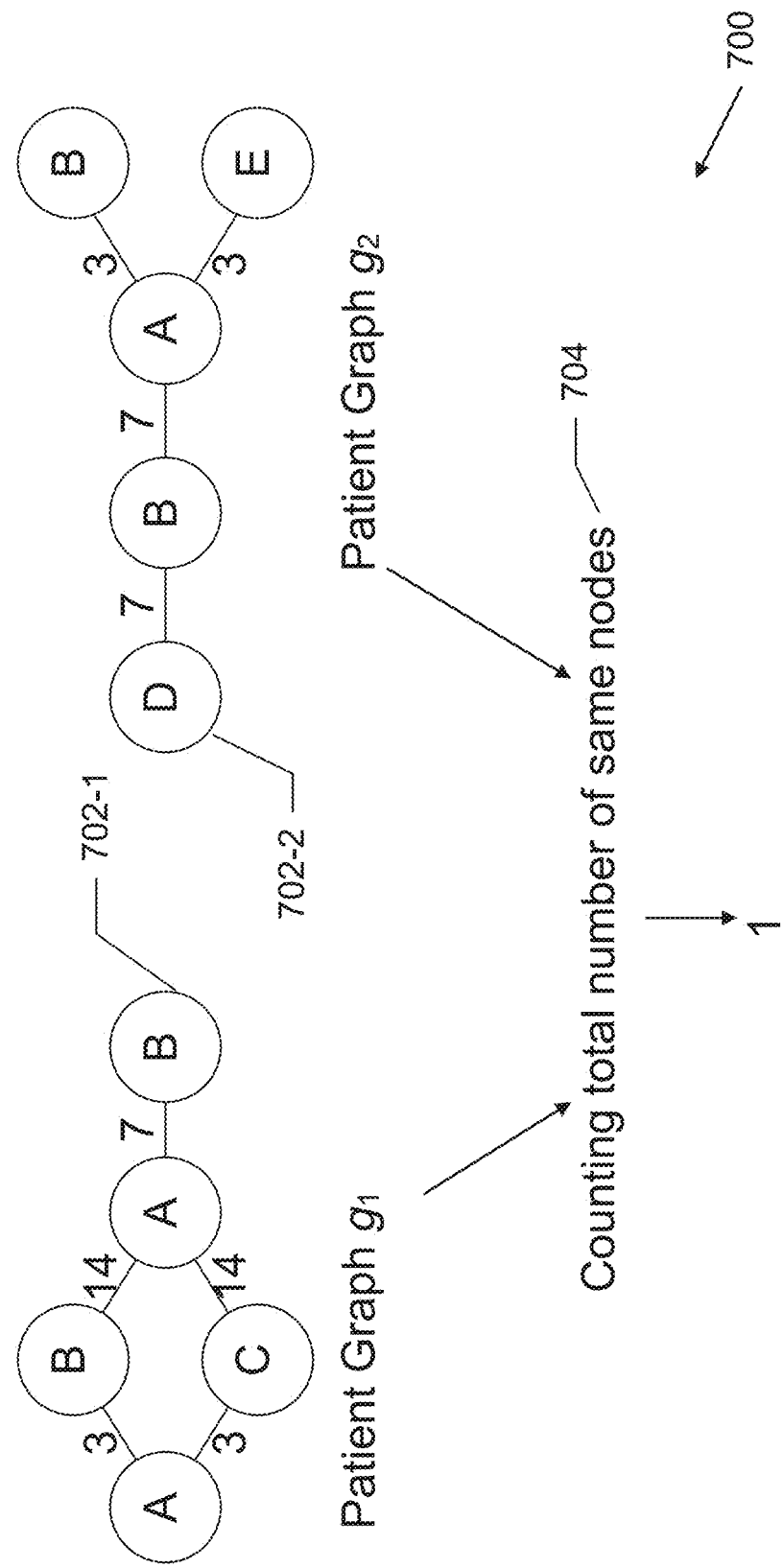
FIG. 7 is an exemplary flow diagram of a process of transferring the input from patient graphs to a node kernel, according to embodiments of the present systems and methods.

An exemplary flow diagram of a process 700 of transferring the input from patient graphs to a node kernel is shown in FIG. 7. As shown in FIG. 7, process 700 begins with patient graphs $g_1$ 702-1, $g_2$ 702-2. At 704, a node kernel $K_{node}$ compares the node labels of two input graphs. The kernel value is the total number of same node labels:

$$K_{node}(g_1, g_2) = \sum_{n_1 \in g_1, n_2 \in g_1, V} K_{label}(n_1, n_2) \quad (13)$$

where $K_{label}$ is defined as:

$$K_{label}(n_1, n_2) = \begin{cases} 1, & \text{if label}(n_1) = \text{label}(n_2) \\ 0, & \text{otherwise} \end{cases} \quad (14)$$

Figure 8:
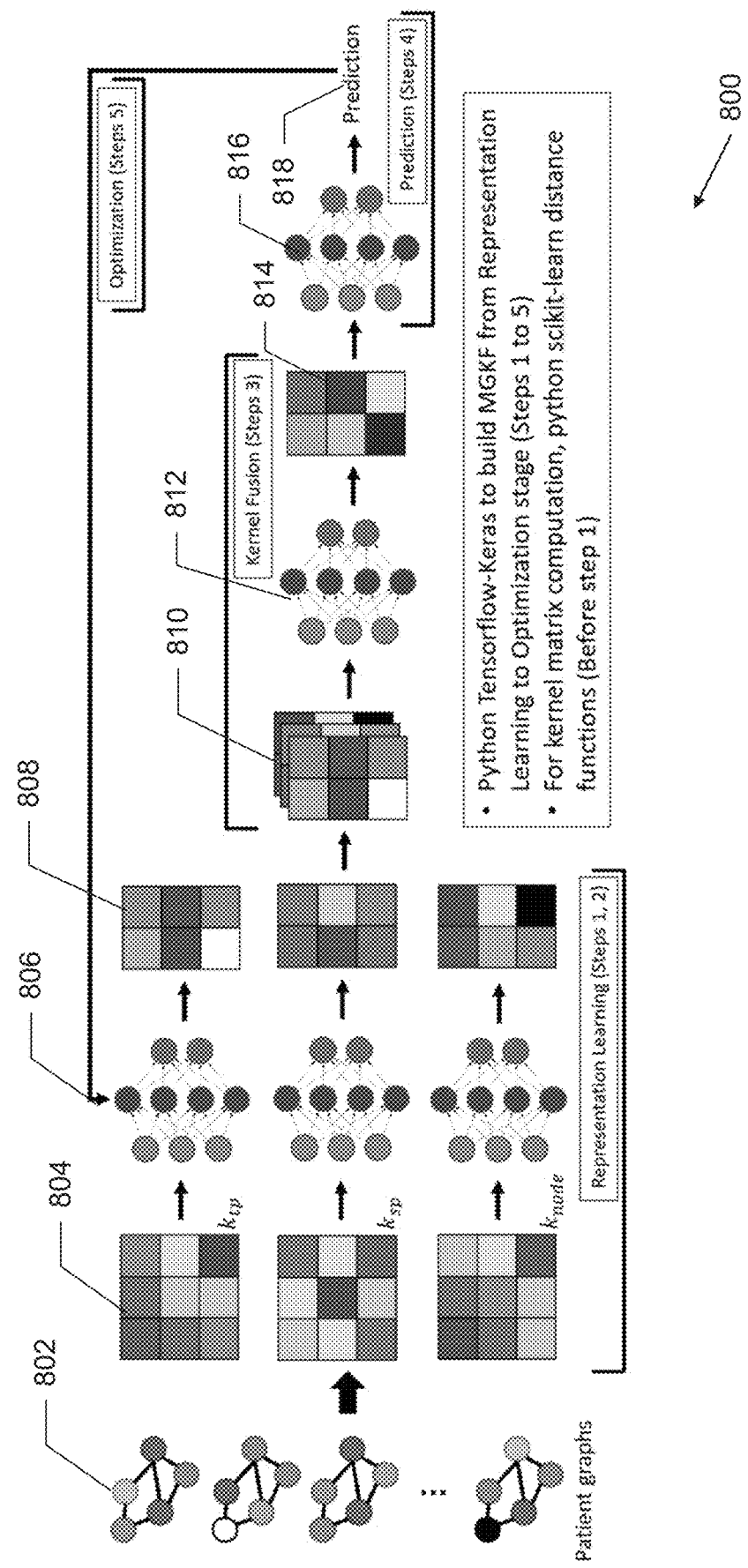
FIG. 8 is an exemplary flow diagram of a process of operation of a multiple graph kernel fusion architecture (MGKF) to perform graph classification, according to embodiments of the present systems and methods.

Embodiments may utilize a multiple graph kernel fusion architecture (MGKF) 800 to perform graph classification, a process of operation of which is shown in FIG. 8. At 802, a plurality of patient graphs may be received/input. At 804, a plurality of kernel gram matrices may be generated. To capture multi-view characteristics on patient graphs, two additional kernels may be used—the shortest path kernel and the node kernel, in conjunction with the temporal proximity kernel. The best combination of these kernels may be found in an end-to-end manner. Specifically, temporal proximity kernel $K_{tp}$ focuses on temporal similarity between substructure such as node ordering and their time difference, shortest path kernel $K_{sp}$ aims to capture similarity in overall connection, and node kernel $K_{node}$ offers a balance between local and global similarity by comparing all node labels between two patient graphs to achieve best accuracy as well as prevent overfitting from noise collaboratively by kernels.

Given kernel gram matrices on all pair of n graphs for each kernel type $K_t \in R^{n \times n}$ where $K_t \, g_i, g_j = k_t(g_i, g_j)$ and $t \in \{tp, sp, node\}$, at 806, a Multi-layer perceptron (MLP) may be used to preform representation learning to generate the corresponding kernel embedding 808 representation $g_{emb} \in R^{n \times m}$ where m<<n. In this case, each row i in $K_t$ represents a high-dimensional feature vector with each dimension being a kernel value (e.g., similarity score) between its associated graph $g_i$ and all other graphs, and its kernel embedding $g_{emb_t}$ can be treated as a dimension reduction by using traditional kernel approximation techniques to generate low dimensional features for $g_i$ such that efficient linear classifier can be used directly, $g_{i_t} \in R^n$ is converted to $g_{emb_t} \in R^m$ under kernel type t as follows.

$$g_{emb_t} = ReLU(W_t g_{i_t} + b_t) \quad (15)$$

by using the kernel embedding weight matrix $W_t \in R^{m \times n}$ and the bias vector $b_t \in R^m$ where n is the number of input graphs, and m is the dimension for the embedding space. The rectified linear unit (ReLU) activation is defined as ReLU (val)=max(val, 0). For deep architecture, the layer l may be computed with its previous layer l−1 with related parameters $W_{tl}$ and $b_{tl}$ within layer by using the same way that we compute the embedding for input kernel gram matrix such as:

$$g_{emb_t}c = ReLU(W_{t_l} g_{emb_{t_{l-1}}} + b_{t_l}) \quad (16)$$

At 810, to combine three kernels, their embeddings 808 from the last layer may be averaged and at 812 may be fused to generate the kernel fusion $g_{emb_F}$ 814 using another dense layer with ReLU activation that learns the kernel fusion $g_{emb_F} \in R^f$:

$$g_{emb_{sum}} = \sum_{t \in \{tp, sp, node\}} g_{emb_{t_{last}}} \quad (17)$$

$$g_{emb_{avg}} = \frac{g_{emb_{sum}}}{3}$$

$$g_{emb_F} = ReLU(W_F g_{emb_{avg}} + b_F)$$

in which $W_F \in R^{f \times q}$ is the fusion weight matrix with fusion embedding dimension f and the bias vector $b_F \in R^f$ assuming the last embedding layer dimension is q.

Further, at 816, the prediction 818 of the label of success or failure for $g_{emb_F}$ may be produced by using a Sigmoid layer defined as:

$$\hat{y} = Sigmoid(W_p g_{emb_F} + b_p) \quad (18)$$

where $W_p \in R^{1 \times f}$ and $b_p \in R$ are trainable weights used to generate class label $\hat{y} \in \{0, 1\}$. A binary cross-entropy loss function may be used to optimize the best embedding under the fusion setting to learn all kernel embedding weight matrices.

In embodiments, each row (for example, each patient) depicts a high dimensional feature vector with each dimension corresponding a kernel value to a specific training example. Since the kernel value can be treated as a similarity measurement, the concept in similarity-based classification may be used, in which class labels are inferred by a set of most similar training examples, and the top k most similar patients may be consulted to get prediction insights based on the nature that features with higher weight contribute more to the result in a linear classifier. Kernel embedding, reducing input dimension, for each kernel type facilitates similarity measurement refinement, reducing the number of training examples used to infer. Similar patients with allied graph similarity may be grouped into one coordinate (e.g., dimension) in the embedding space.

Since kernel embedding space is trained in an end-to-end manner through ReLU operation in Equation 16, which achieves the interpretability, a set of candidates may be selected that contribute most to the prediction, via top k value coordinates in the embedding space. The selected ones under different kernel type can be interpreted as multi-view representative cases (such as time propagation or disease connection) in case-based learning. In practice, patient $g_{emb_t}$ may be sorted in kernel embedding space, and the top k coordinates may be selected. The top k' training examples for the i-th coordinate in top k coordinates may be selected. All sorts are in a reverse order:

$$argsort(g_{emb_t})[1:k] \quad (19)$$

$$argsort(W_t[i, :])[1:k'] \quad (20)$$

Figure 9:
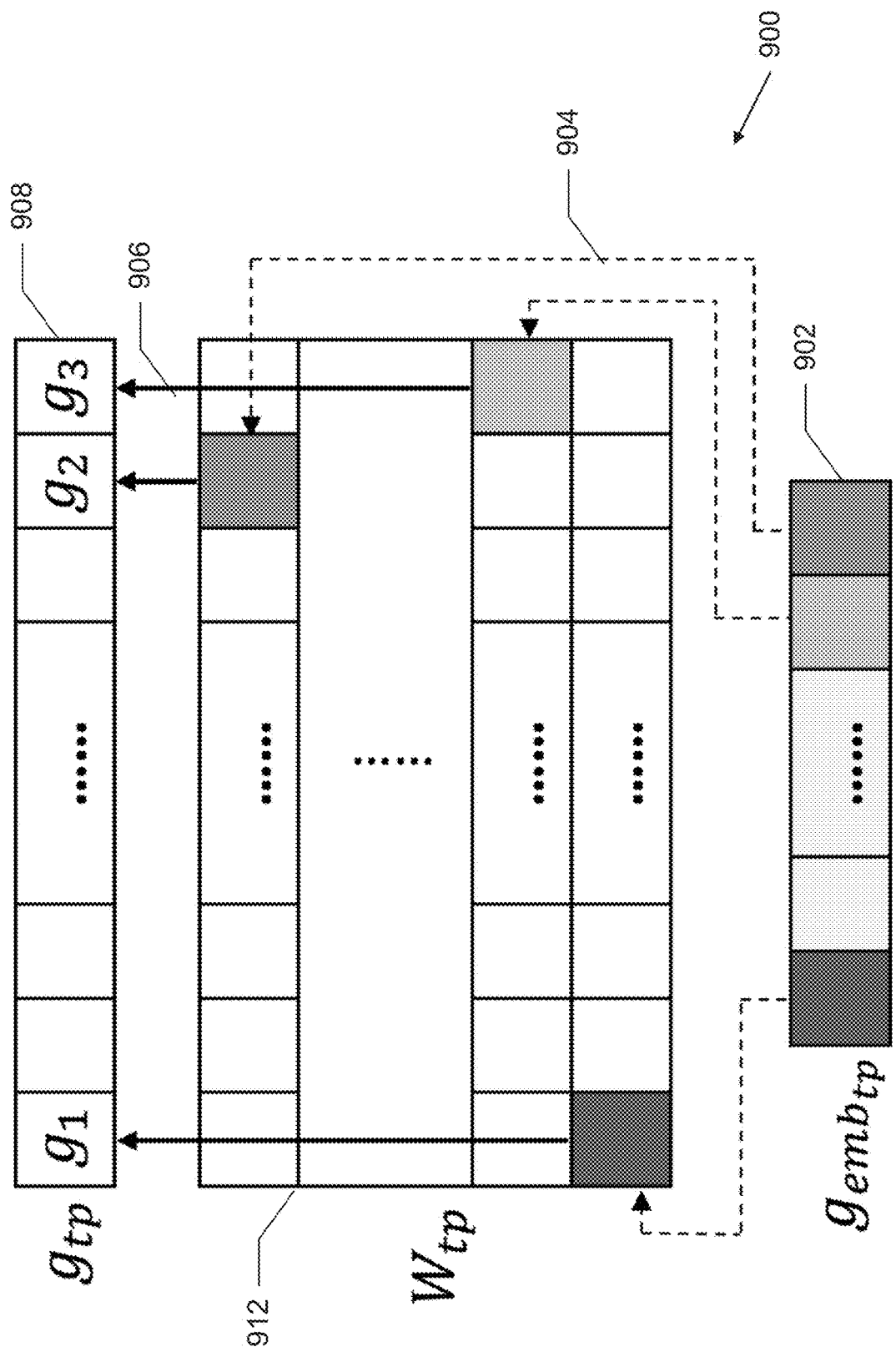
FIG. 9 is an exemplary flow diagram of a process of interpretation, according to embodiments of the present systems and methods.

An exemplary process 900 of interpretation is shown in FIG. 9. Given an embedded patient vector $g_{emb_{tp}}$ 902, at 904, it may be sorted in a descending order and, for example, the top three value dimensions may be selected. At 906, the training examples in $g_{tp}$ 908, which contribute most may be found, through weight matrix $W_{tp}$ 912.

Figure 10:
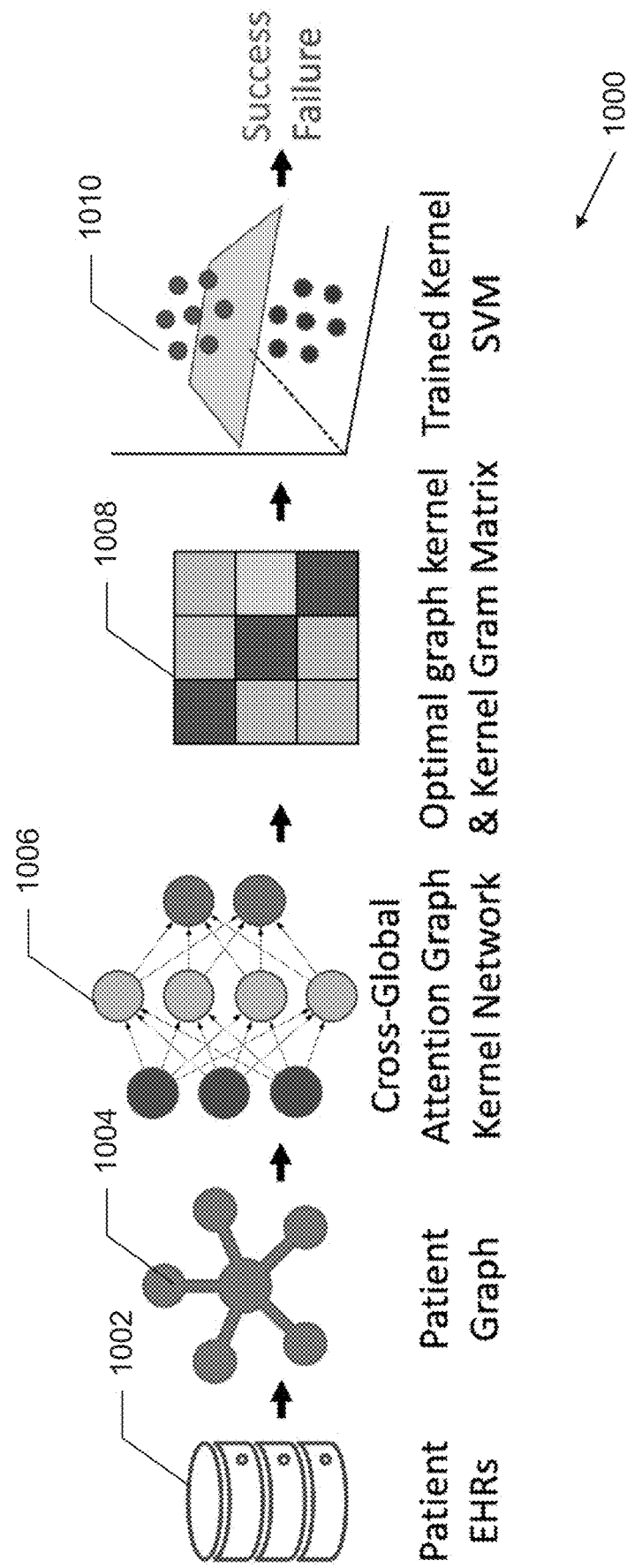
FIG. 10 is an exemplary illustration of a predictive framework directed to predicting effectiveness of a course of treatment for a chronic condition, according to embodiments of the present systems and methods.

An exemplary embodiment of a predictive framework 1000 directed to predicting effectiveness of a course of treatment for a chronic condition is shown in FIG. 10. Predictive framework 1000 may include information relating to a patient 1002, such as patient EHRs, which may be used to generate a patient graph 1004, as described above. Patient graph 1004 may be used to generate a Cross-Global Attention Graph Kernel Network 1006, which may be used to generate an optimal graph kernel and Kernel Gram Matrix 1008 which may be used to generate a trained Kernel SVM 1010, which may be used to predict effectiveness of the course of treatment.

Embodiments may formulate the prediction task as a binary graph classification on graph-based EHRs 1004 using a kernel SVM 1010. Such embodiments may learn a graph kernel. Given a set of success and failure case patient graphs G, a deep neural network may learn an optimal graph kernel k. Then, the prediction for success or failure is performed by a kernel SVM 1010 using a kernel gram matrix K 1008 such that $K_{ij}=k(G_i,G_j)$ where $G_i, G_j \in G$. For an incoming patient, a patient graph $G_p$ 1004 may be created based on the concatenation of patient's medical history, current diagnosis, and treatment plan. Then, the kernel value between Gp and all training examples $G_i \in G$ may be determined, and prediction may be performed through a kernel SVM 1010, as shown in FIG. 10.

Figure 11:
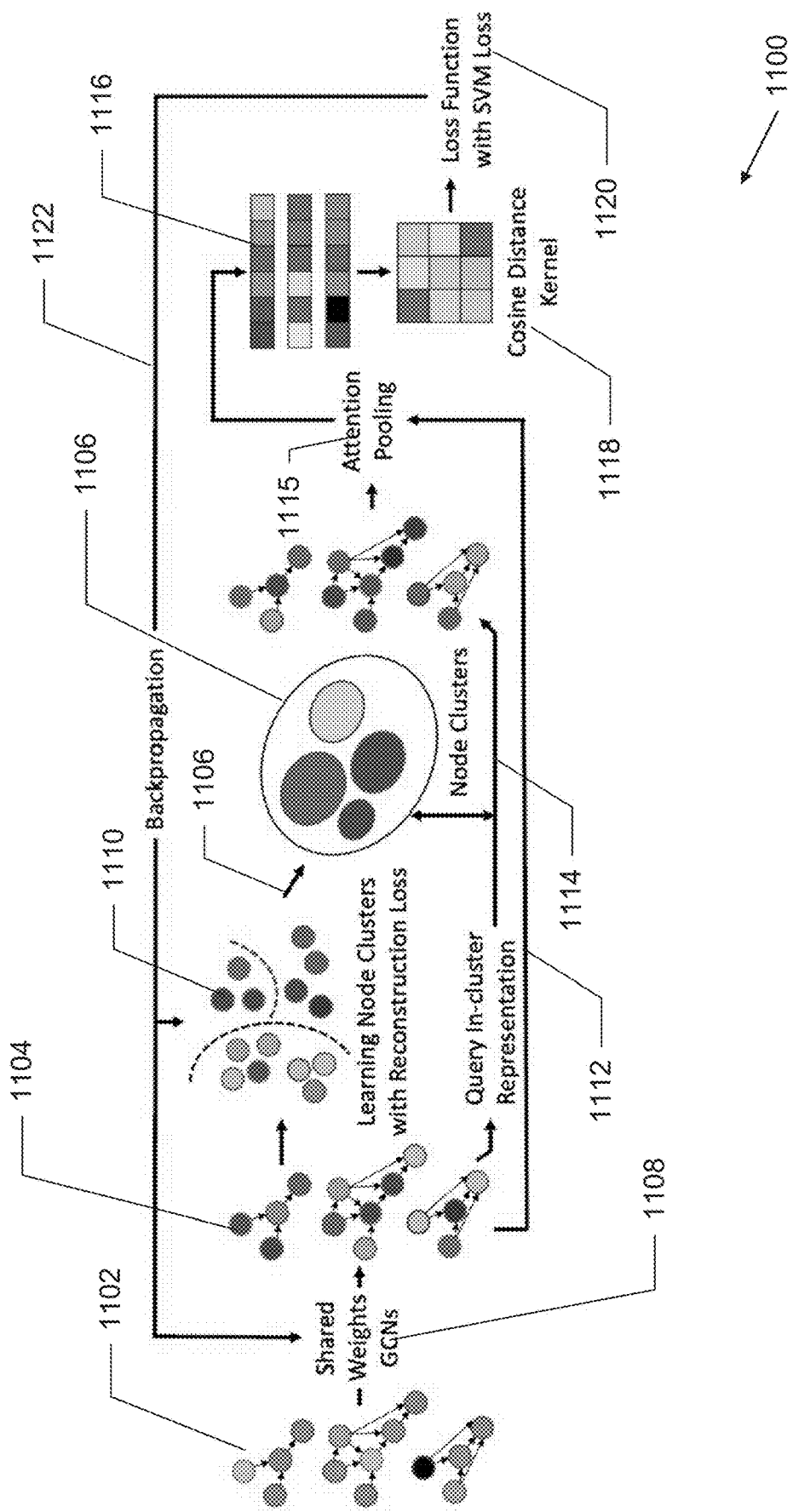
FIG. 11 is an exemplary illustration of a Cross-Global Attention Graph Kernel Network learning an end-to-end deep graph kernel on a batch of graphs, according to embodiments of the present systems and methods.

In embodiments, a Cross-Global Attention Graph Kernel Network 1100 may learn an end-to-end deep graph kernel on a batch of graphs, as shown in FIG. 11. At 1102, a plurality of patient graphs may be received/input. The node level embedding 1104 and node clusters 1106 may be determined first by, at 1108 determining shared weight Graph Convolutional Networks (GCNs) to form node level embedding 1104, and at 1110, determining learning node clusters with reconstruction loss to form node clusters 1106. The graph level embedding may be derived 1112 from node matching 1114 based attention pooling 1115. The loss 1120 may be calculated 1116 by the resulting distance and kernel matrix 1118 and backpropagation 1122 may be performed to update all model parameters.

As shown, this may be accomplished through cross-global attention node matching without an explicit pairwise similarity computation. Given a batch B of input graphs $G_1, \ldots, G_{|B|}$ with batch size |B|, their nodes may be embedded into a lower dimensional space, where node structures and attribute information are encoded in dense vectors. A graph level embedding may then be produced by a graph pooling operation on node level embedding via cross-global attention node matching. The batchwise cosine distance may be calculated and a kernel gram matrix may be generated on the entire batch of resulting graph embedding. Finally, the network loss may be computed with contrastive loss, kernel alignment, and SVM primal objective.

Embodiments may perform Graph Embedding using Graph Convolutional Networks. Graph Convolutional Networks (GCN) may perform 1-hop neighbor feature aggregation for each node in a graph. The resulting graph embedding is permutation invariant when a pooling operation is properly chosen. Given an n number of nodes patient graph G with node attribute one-hot vector matrix $X \in R^{n \times c}$, where c denotes the total number of medical codes in EHRs, and a weighted adjacency matrix $A \in R^{n \times n}$, GCN may be used to generate a node level embedding $H \in R^{n \times d}$ with embedding size $d \in R$ as follows:

$$H = f(\tilde{D}^{-1} \tilde{A} X W)$$

where $\tilde{D}$ is the diagonal node degree matrix of $\tilde{A}$ defined with $\tilde{D}=\Sigma j \tilde{A}_{ij}$, $\tilde{A}=A+I$ is the adjacency matrix with self-loops added, $W \in R^{c \times d}$ is a trainable weight matrix, and f is a non-linear activation function such as ReLU (x)=max (0, x). The embedding H can be an input to another GCN, creating stacked multiple graph convolution layers:

$$H^{k+1} = f(\tilde{D}^{-1} \tilde{A} H^k W^k), H^0 = X \qquad (22)$$

where $H^k$ is the node embedding after the $k^{th}$ GCN operation, and $W^k$ is the trainable weight associated with the $k^{th}$ GCN layer. The resulting node embedding $H^{k+1}$ contains k-hop neighborhood structure information aggregated by graph convolution layers.

Embodiments may perform graph embedding using higher-order graph information. To capture longer distance nodes and their hierarchical multi-hop neighborhood information, t multiple GCN layers may be stacked and all layer's outputs $H^{1:t}=[H^1, \ldots, H^t]$ concatenated, where $H^{1:t} \in R^{n \times (t \times d)}$. The concatenated node embedding might be very large and could potentially cause a memory issue for subsequent operations. To mitigate such drawbacks, we perform a non-linear transformation on $H^{1:t}$ by a trainable weight $W_{concat} \in R^{(t \times d) \times d}$ and a ReLU activation function as follows:

$$H_{final} = ReLU(H^{1:t} W_{concat}) \qquad (23)$$

To produce the graph level embedding, instead of using another type of pooling operation, embodiments may use cross-global attention node matching and its derived attention based pooling.

Cross-Global Attention Node Matching between graphs may be computed via a pairwise node similarity measurement. This optimizes a distance metric-based or KL-divergence loss on the graph pairs or triplets necessitating vast training pairs or triplets to capture the entire global characteristics. One way to avoid explicit pair or triplet generation utilizes efficient batch-wise learning via optimizing classification loss. However, pairwise node matching in a batch-wise setting is problematic due to graph size variability. To address this issue, one may use a batch-wise attention-based node matching scheme, also known as cross-global attention node matching. The matching scheme may learn a set of global node clusters and may compute the attention weight between each node and the representation associated with its membership cluster. The pooling operation based on its attention score to global cluster may perform a weighted sum on nodes to derive a single graph embedding.

Figure 12:
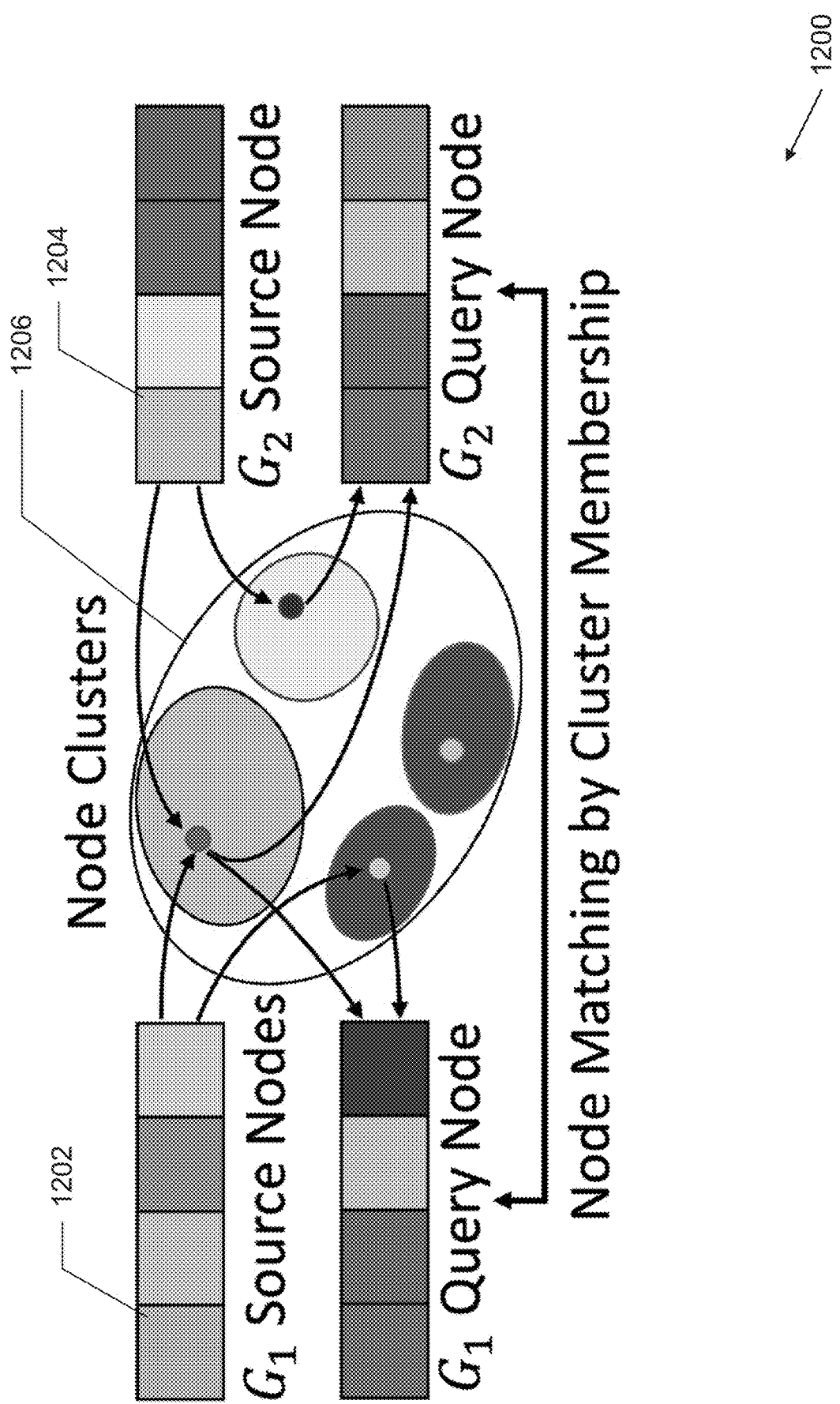
FIG. 12 is an exemplary illustration of matching by retrieving cluster identity from global node clusters, according to embodiments of the present systems and methods.

Given node embedding $H_{final} \in R^{n \times d}$ from the last GCN layer and transformation after concatenation in Equation 23, define $M \in R^{s \times d}$ as a trainable global node cluster matrix with s clusters and d dimension features sized to provide an overall representation of its membership nodes. Here, define membership assignment $A \in R^{n \times s}$ for $H_{final}$ and as follows:

$$A = Sparsemax(ReLU(H_{final} M^T)) \qquad (24)$$

where Sparsemax is a sparse version Softmax, that outputs sparse probabilities. It can be treated as a sparse soft cluster assignment. A may be interpreted as a cluster membership identity with s dimension feature representation. Further define the query of nodes' representation in their belonging membership cluster:

$$Q = Tanh(AM) \qquad (25)$$

where $Q \in R^{n \times d}$ denotes a queried representation for each node in $H_{final}$ from their belonging membership cluster. As shown in FIG. 12, matching can be treated as retrieving cluster identity from global node clusters, and similar nodes are assigned to a similar or even the same cluster membership identity. To construct a better cluster, we add an auxiliary loss by minimizing the reconstruction error $L_{recon}=\|H_{final}-Q\|F$, which is similar to Non-negative Matrix Factorization (NMF) clustering.

Embodiments may utilize Pooling with Attention-based Node Matching. The intuition of pairwise node matching is to assign higher attention-weight to those similar nodes. In other words, matching occurs when two nodes are highly similar, closer to each other than to other possible targets. Following this idea, it is observed that two nodes are matched if they have similar or even identical cluster membership. The higher the similar membership identity, the higher the degree of node matching. In addition, a cluster is constructed by minimizing the reconstruction error between the original node $H_{final}$ and the query representation Q. A node with high reconstruction error means no specific cluster assignment and further lowers the chance to match other nodes. This can be measured by using similarity metrics (e.g., cosine similarity) between $H_{final}$ and Q. Based on these observations, cross-global attention node matching pooling may be designed, wherein a node similar to the representation in its cluster membership should receive higher attention weight, as follows:

$$a = Softmax(Sim(H_{final}, Q)) \quad (26)$$

$$G_{emb} = \sum_{i=1}^{n} a_i H_{final_i} \quad$$

where $\alpha \in R^n$ is the attention weight for each node, Softmax is applied to generate importance among nodes by using Sim, a similarity metric (e.g., cosine similarity), and the resulting pooling $G_{emb}$ is the weighted sum of node embeddings that compress higher order structure and node matching information from other graphs.

Matching and cluster assignment membership is illustrated in FIG. 12, which shows a predictive framework 1200. Each node in $G_1$ 1202, $G_2$ 1204 may map to a cluster 1206. Their cluster membership assignments may generate their query, which is their representation in terms of belonging to a cluster. Such an assignment may be seen as a soft label of cluster membership identity. Similar query means similar cluster membership identity, inducing possible matching.

Graph Kernel. Given a graph pair with their graph level embeddings $G_{emb_1}$, $G_{emb_2}$, the graph kernel may be defined as follows:

$$Dist_C(G_{emb_1}, G_{emb_2}) = 1 - \frac{G_{emb_1} \cdot G_{emb_2}}{\|G_{emb_1}\|\|G_{emb_2}\|} \quad (27)$$

$$Dist_E(G_{emb_1}, G_{emb_2}) = \|G_{emb_1} - G_{emb_2}\|_2$$

$$K(G_{emb_1}, G_{emb_2}) = \exp(-Dist(G_{emb_1} - G_{emb_2})^2)$$

where $Dist_C$ is a cosine distance and $Dist_E$ is the Euclidean distance. Dist can be either $Dist_C$ or $Dist_E$. The resulting kernel function is positive definite since exp(-x) is still positive definite for any non-negative real number x. Cosine distance enjoys benefits in more complex data representations. Euclidean distance considers vector magnitude (such as the norm) during measurement which is not sufficiently sensitive to highly variant features such as long-term disease progressions. Moreover, cosine distance can measure objects on manifolds with nonzero curvature such as spheres or hyperbolic surfaces. In general, Euclidean distance can only be applied to local problems which may not be sufficient to express complex feature characteristics. The resulting cosine guided kernel is more expressive, and thus, capable of performing implicit high dimensional mapping. Note that the use of other distance functions that support a positive definitive kernel is likewise within the scope of this disclosure.

Given a batch B of input graphs and their class labels $y \in R^{|B| \times 1}$ where $y_i \in \{1, 0\}$, we get their graph level embeddings for the entire batch via shared weight GCN with cross-global node matching pooling. Then, we calculate their batch-wise distance matrix $D \in R^{|B| \times |B|}$ and batch-wise kernel gram matrix $K \in R^{|B| \times |B|}$. The model can be trained by mini-batch Stochastic Gradient Descent (SGD) without training pair and triplet generation. To learn an optimal graph embedding, which results in an optimal graph kernel, we optimize it by contrastive loss with a margin threshold $\lambda > 0$ and kernel alignment loss:

$$\mathcal{L}_{contrastive} = \frac{1}{|B|} \sum_{i,j \in B} (1 - Y_{ij}) \max(0, \lambda - D_{ij})^2 + Y_{ij} D_{ij} \quad (28)$$

and kernel alignment loss:

$$\mathcal{L}_{alignment} = \frac{1}{|B|} \sqrt{2 - 2 \langle\langle K, Y \rangle_F / \sqrt{\langle K, K \rangle_F \langle Y, Y \rangle_F}} \quad (29)$$

where $\langle \cdot, \cdot \rangle_F$ denotes the Frobenius inner product, K is a batch-wise kernel gram matrix, and $Y \in R^{|B| \times |B|}$ where $Y_{ij}=1$ if $y_i=y_j$ else $Y_{ij}=0$. A good distance-metric may induce a good kernel function and vice versa. So, the graph kernel may be learned jointly through optimal cosine distance between graphs via contrastive loss with an optimal graph kernel through kernel alignment loss:

$$\mathcal{L}_{kernel} = \mathcal{L}_{contrastive} + \mathcal{L}_{alignment} \quad (30)$$

To align a learned embedding, distance, and kernel to the classification loss in end-to-end training, the SVM primal objective may be incorporated with a squared hinge loss function into the objective:

$$\mathcal{L}_{SVM} = C \sum_{i,j \in B} \beta_i \beta_j K_{ij} + \sum_i \max\left(0, 1 - y_i \sum_{j \in B} K_{ij} \beta_j\right)^2 \quad (31)$$

where $C >= 0$ is a user defined inverse regularization constant and $\beta \in R^{|B| \times \times 1}$ is a trainable coefficient weight vector. The following is the final model optimization problem formulation:

$$\min_{\theta, \beta} \frac{\mathcal{L}_{kernel}}{\theta} + \frac{\mathcal{L}_{recon}}{\theta} + \frac{\mathcal{L}_{SVM}}{\beta} \quad (32)$$

where $\theta$ denotes a set of all trainable variables in graph embedding and $\beta$ is a trainable coefficient weight vector for SVM. Since the training is done by mini-batch SGD, the SVM objective is only meaningful for a given batch. Namely, gradient for β in SVM are only relevant for the current batch update as the SVM objective is dependent on the input kernel gram matrix. When training proceeds to the next batch, the kernel gram matrix is different, and the optimized β is inconsistent with the last batch status. To resolve this inconsistent weight update problem, treat SVM as a light-weight auxiliary objective (e.g., regularization), encouraging the model to learn an effective graph kernel. In this case, first perform a forward pass through graph kernel network, then train the SVM by feeding in the kernel gram matrix from the forward pass output until convergence. The positive definiteness of the kernel function guarantees SVM convergence. Once the SVM is trained, treat β as a model constant, and $\mathcal{L}_{SVM}$ now acts as a regular loss function. The gradient of θ can be computed through $\mathcal{L}_{kernel}$, $\mathcal{L}_{recon}$, and $\mathcal{L}_{SVM}$, and the model can perform backpropagation to update θ.

Figure 15:
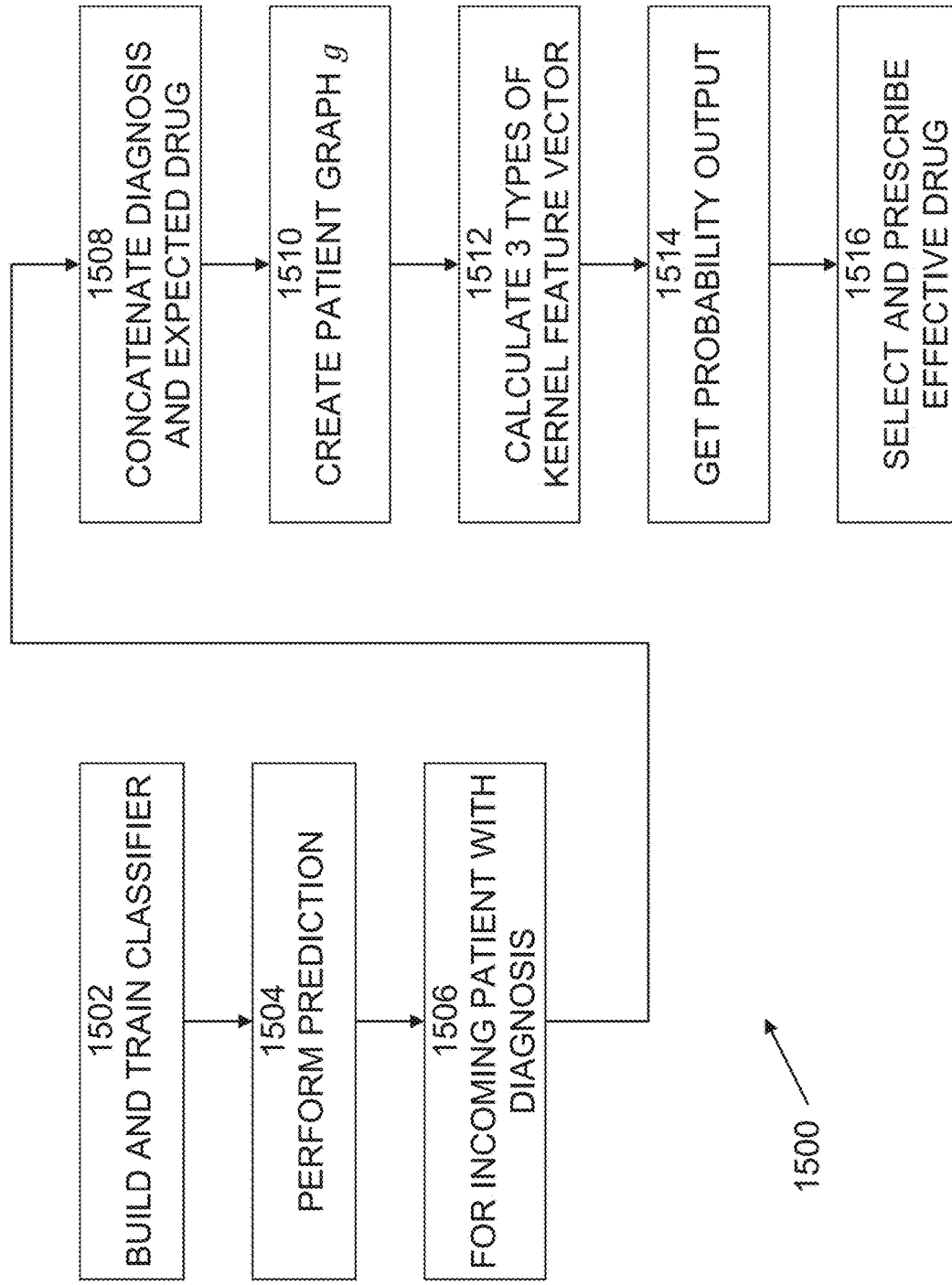
FIG. 15 is an exemplary flow diagram of a process for prediction for outcome of a drug prescription, according to embodiments of the present systems and methods.

An exemplary process 1500 for predicting the outcome of a drug prescription is shown in FIG. 15. Process 1500 begins with 1502, in which a classifier with an MGKF framework may be built and trained for each type of disease. Typically, training may be performed using only patients with that type of disease to train the MGKF. At 1504, to complete the training, the trained classifiers may be used with an MGKF framework to perform prediction for each type of disease. At 1506, for an incoming patient with a diagnosis, at 1508 the diagnosis and the expected drug prescription may be concatenated to the patient's medical history (if any). At 1510, a patient graph g may be created. At 1512, three types of kernel feature vectors, for a Temporal Proximity Kernel, a Shortest Path Kernel, and a Node Kernel, may be calculated between g and all training examples. At 1514, a probability output may be obtained using the MGKF with same disease diagnosis type. For example, a probability output>0.5 may mean possible failure. At 1516, a drug or treatment that is likely to be effective, based on the probability output for that drug or treatment may be selected and prescribed to a patient.

Figure 16:
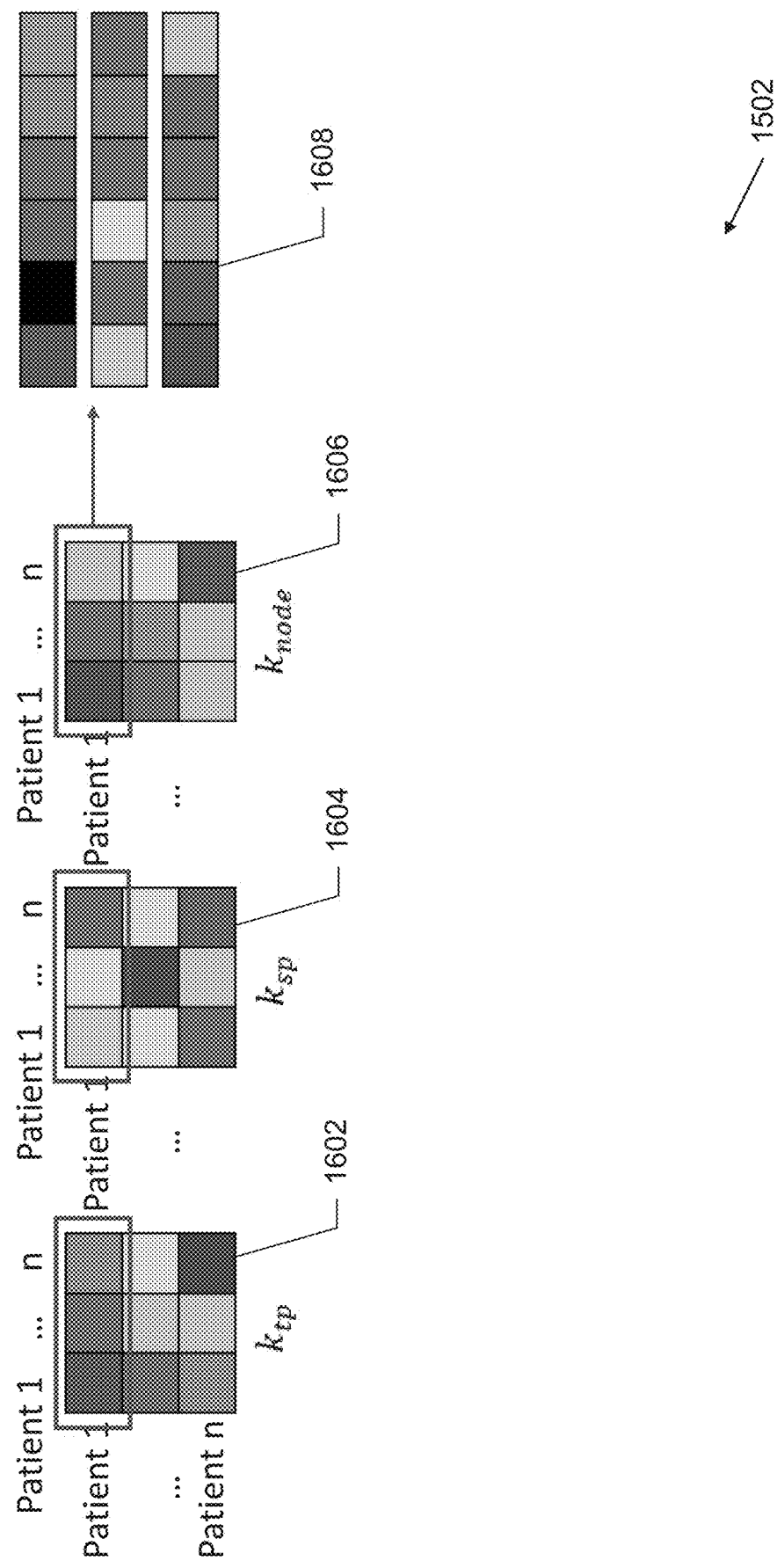
FIG. 16 is an exemplary flow diagram of a process of training a classifier with an MGKF framework, according to embodiments of the present systems and methods.

An exemplary process 1502 of training a classifier with an MGKF framework is shown in FIG. 16. Given n patient graphs under specific type of disease for example, a UTI, an nxn kernel gram matrix may be created for each of $k_{tp}$, $k_{sp}$, and $k_{node}$. Each row represents an n dimension feature vector for each associated patient and describes the similarity (kernel value) to all n patients. In this example, there are n patients with each patient having an n dimensional feature vector in $k_{tp}$, $k_{sp}$, and $k_{node}$. Each row in $k_{tp}$, $k_{sp}$, and $k_{node}$ may be treated as a one-dimensional feature vector 1608.

Figure 17:
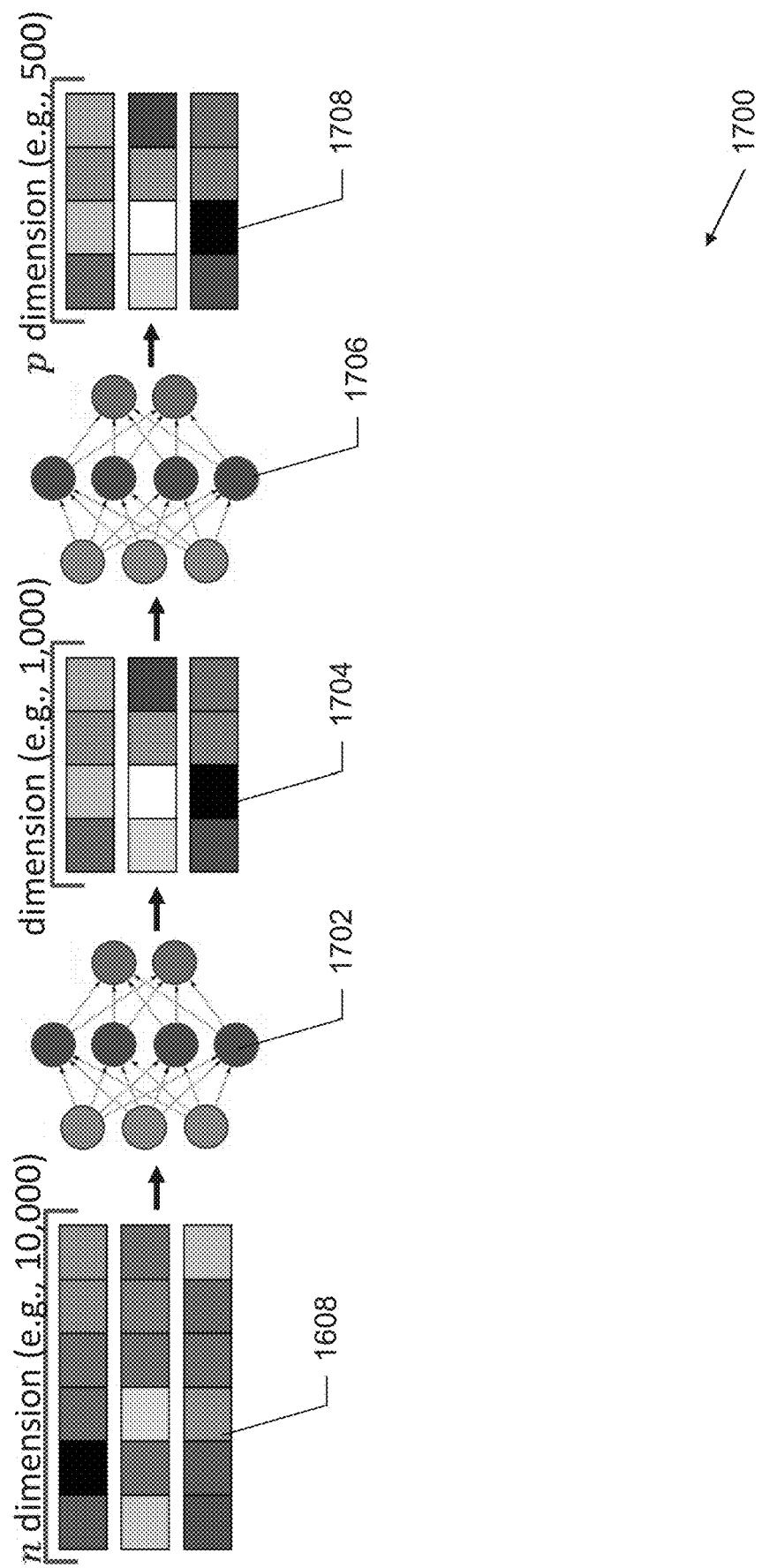
FIG. 17 is an exemplary flow diagram of a portion of a process of using the trained classifiers with an MGKF framework to perform prediction for each type of disease, according to embodiments of the present systems and methods.
Figure 18:
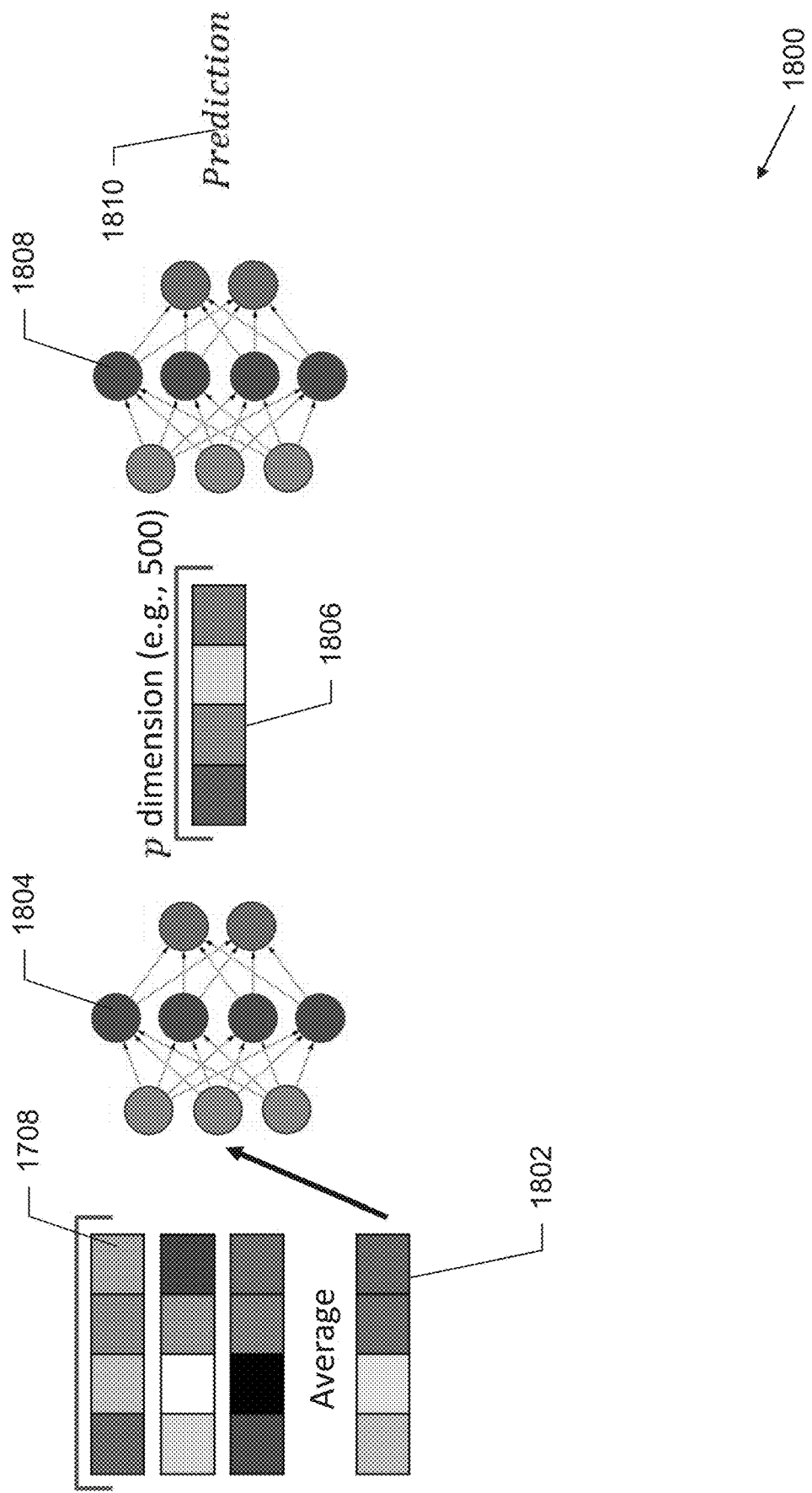
FIG. 18 is an exemplary flow diagram of a portion of a process of using the trained classifiers with an MGKF framework to perform prediction for each type of disease, according to embodiments of the present systems and methods.

An exemplary process 1504, of using the trained classifiers with an MGKF framework to perform prediction for each type of disease is shown in FIGS. 17 and 18. The three types of feature vectors (vector of kernel values 1608) may be input into an MGKF framework to generate predictions. A portion (representation learning) 1700 of exemplary process 1504 is shown in FIG. 17. For each n dimensional feature vector 1608 from $k_{tp}$, $k_{sp}$, and $k_{node}$, MLP 1702 may be used to reduce the dimension from n to m. For example, at 1702 each type of feature vector may be embedded with a dimension size 10,000 to 1,000 1704 via a single layer MLP with ReLU activation (1,000 hidden size). At 1706, for each type of embedding, the dimension may, for example, be reduced from 1,000 to 500 via a 3 layer MLP with ReLU activation (hidden size for 800, 600, and 500 for each layer) to get a final representation 1708.

A portion (Kernel Fusion and Prediction) 1800 of exemplary process 1504 is shown in FIG. 18. After final representation learning (embedding) 1708 for each type of feature vectors, the feature vectors may be averaged to form a single vector and input into a single layer MLP (500 hidden size) 1804 to learn the final representation 1806. At 1808, another MLP, such as a single layer (1 hidden size) MLP with sigmoid activation may be used to output probability 1810 of likelihood for success or failure.

Figure 19:
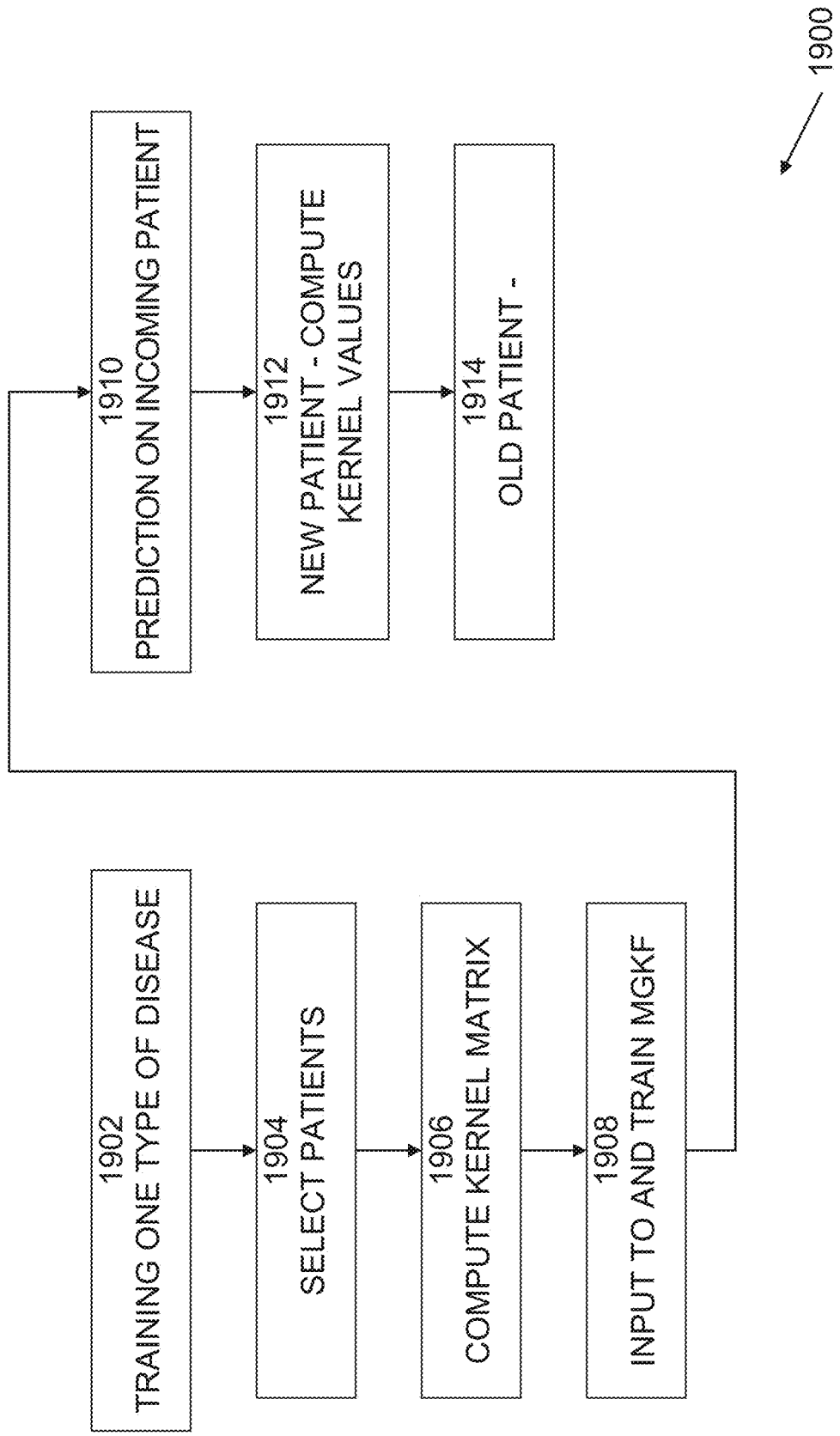
FIG. 19 is an exemplary flow diagram of a process of predicting drug and/or treatment outcomes, according to embodiments of the present systems and methods.

An exemplary process of predicting drug and/or treatment outcomes is shown in FIG. 19. Process 1900 begins with 1902, in which, for training for one type of disease, at 1904, n patients, for example, 10,000, may be selected under selected disease types as training examples, and their patient graphs may be created. At 1906, a pairwise kernel matrix under each type of kernel, a Temporal Proximity Kernel, a Shortest Path Kernel, and a Node Kernel, may be computed, for all patients. At 1908, the pairwise kernel matrix may be input to train the MGKF. At 1910, predictions for incoming patients may be generated. At 1912, if the patient is anew patient, that is, not included in the training examples, then the kernel values between the graph of the new patient and all training examples may be computed. If the patent is an old patient, that is, included in the training examples, then return the entire patient's belonging row in the kernel gram matrix $k_{tp}$, $k_{sp}$, and $k_{node}$. It may be noted that there is no need to retrain when there is a sufficiently large number of training examples.

Figure 20:
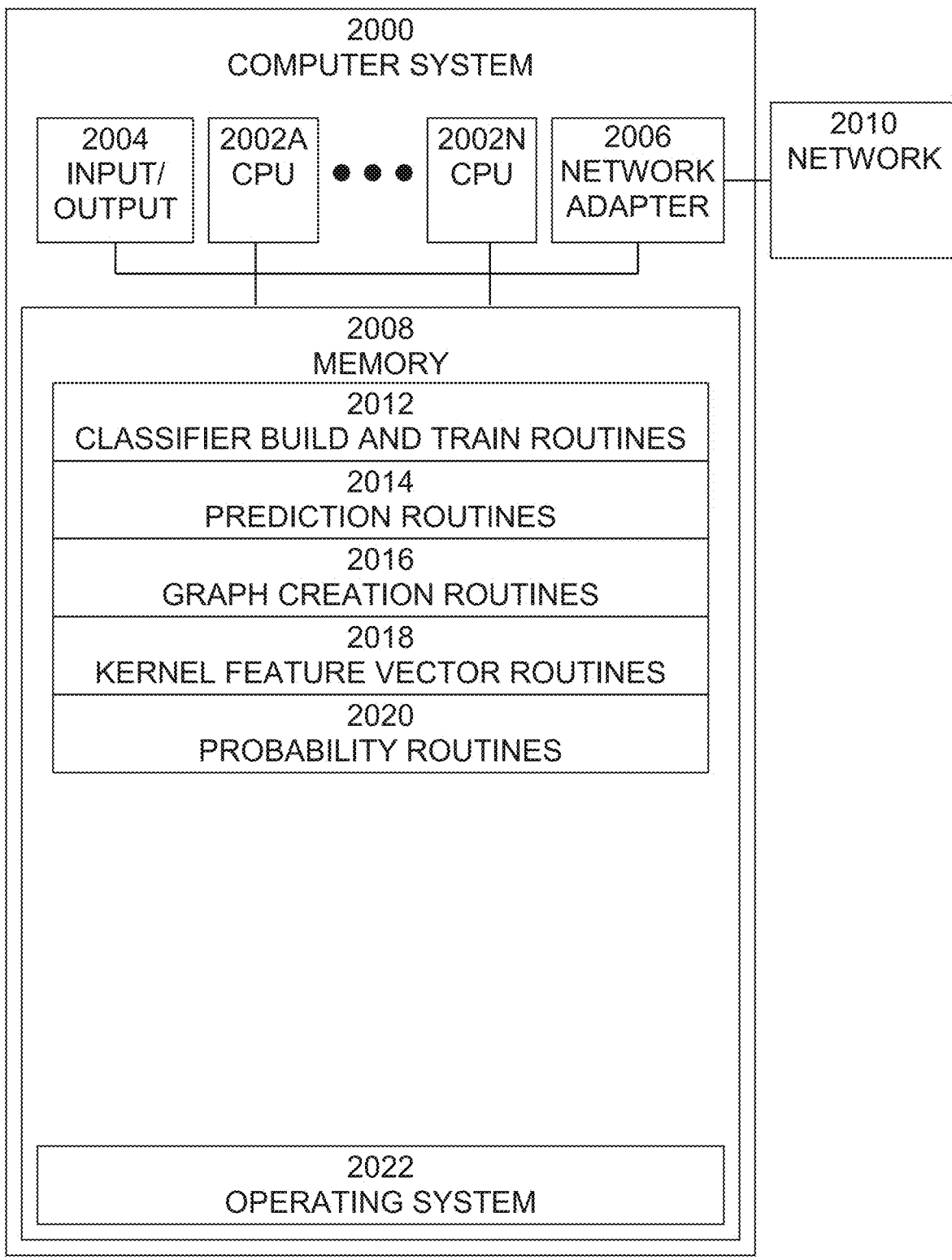
FIG. 20 is an exemplary block diagram of a computer system, in which processes involved in the embodiments described herein may be implemented.

An exemplary block diagram of a computer system 2000, in which processes involved in the embodiments described herein may be implemented, is shown in FIG. 20. Computer system 2000 may be implemented using one or more programmed general-purpose computer systems, such as embedded processors, systems on a chip, personal computers, workstations, server systems, and minicomputers or mainframe computers, or in distributed, networked computing environments. Computer system 2000 may include one or more processors (CPUs) 2002A-2002N, input/output circuitry 2004, network adapter 2006, and memory 2008. CPUs 2002A-2002N execute program instructions in order to carry out the functions of the present communications systems and methods. Typically, CPUs 2002A-2002N are one or more microprocessors, such as an INTEL CORE® processor. FIG. 20 illustrates an embodiment in which computer system 2000 is implemented as a single multi-processor computer system, in which multiple processors 2002A-2002N share system resources, such as memory 2008, input/output circuitry 2004, and network adapter 2006. However, the present communications systems and methods also include embodiments in which computer system 2000 is implemented as a plurality of networked computer systems, which may be single-processor computer systems, multi-processor computer systems, or a mix thereof.

Input/output circuitry 2004 provides the capability to input data to, or output data from, computer system 2000. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 2006 interfaces device 2000 with a network 2010. Network 2010 may be any public or proprietary LAN or WAN, including, but not limited to the Internet.

Memory 2008 stores program instructions that are executed by, and data that are used and processed by, CPU 2002 to perform the functions of computer system 2000.

Memory 2008 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 2008 may vary depending upon the function that computer system 2000 is programmed to perform. In the example shown in FIG. 20, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present communications systems and methods may include any and all such arrangements.

In the example shown in FIG. 20, memory 2008 may include classifier build and train routines 2012, prediction routines 2014, graph creation routines 2016, kernel feature vector routines 2018, probability routines 2020, and operating system 2022. Classifier build and train routines 2012 may include software to build and train a classifier with an MGKF framework for each type of disease, as described above. Prediction routines 2014 may include software to use the trained classifiers with an MGKF framework to perform prediction for each type of disease, as described above. Graph creation routines 2016 may include software to create patient graphs, as described above. Kernel feature vector routines 2018 may include software to calculate three types of kernel feature vectors, a Temporal Proximity Kernel, a Shortest Path Kernel, and a Node Kernel, between each patient graph and all training examples, as described above. Probability routines 2020 may include software to generate a probability output using the MGKF with same disease diagnosis type, as described above. Operating system 2022 may provide additional system functionality.

As shown in FIG. 20, the present communications systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multi-tasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method of computing a probable drug efficacy implemented in a computer system comprising a processor, memory accessible by the processor and storing computer program instructions and data, and computer program instructions to perform:
    for a plurality of patients, generating and storing in the memory a directed acyclic graph representing health events of each patient, each directed acyclic graph comprising:
        a first node representing demographic information of the patient,
        a plurality of additional nodes, each additional node representing a medical event of the patient,
        at least one first edge connecting the first node to an additional node, and
        a plurality of additional edges, each additional edge connecting nodes representing two consecutive medical events, the edge having a weight based on a time difference between the two consecutive medical events;
    capturing, using the processor, a plurality of features from each directed acyclic graph stored in the memory;
    training a classifier model using a plurality of the captured features of each directed acyclic graph;
        applying the classifier model to determine a probability that a drug or treatment will be effective for a particular patient; and
    determining, using the processor, a drug or treatment to be prescribed to the particular patient based on the determined probability.

2. The method of claim 1, wherein the classifier model comprises a deep learning model.

3. The method of claim 2, wherein the deep learning model comprises a neural network.

4. The method of claim 1, The method of claim 1, wherein the plurality of features are captured by:
    transforming each directed acyclic graph to a shortest path graph;
    generating a temporal topological kernel by recursively calculating similarity among temporal ordering on a plurality of groups of additional nodes; and
    generating a temporal substructure kernel on additional edges connecting additional nodes in each group of additional nodes.

5. The method of claim 1, wherein the plurality of features are captured by:
    generating a topological ordering of each directed acyclic graph based on an order of occurrence of a label associated with each additional node in each directed acyclic graph;

generating a topological sequence of each directed acyclic graph comprising a plurality of levels indicating an order of occurrence of a same node label in the topological sequence;
generating a temporal signature for each directed acyclic graph comprising a series of total passage times from the first node to each additional node in a union of a plurality of topological sequences;
generating a temporal proximity kernel between a plurality of pairs of temporal signatures;
generating a shortest path kernel by calculating an edge walk similarity on shortest path graphs for a plurality of pairs of directed acyclic graphs;
generating a node kernel by comparing node labels of a plurality of pairs of directed acyclic graphs; and
fusing the temporal proximity kernel, the shortest path kernel, and the node kernel.

6. The method of claim 5, wherein the fusing comprises:
reducing dimensions of the temporal proximity kernel, the shortest path kernel, and the node kernel for the plurality of pairs of directed acyclic graphs; and
averaging embeddings of the temporal proximity kernel, the shortest path kernel, and the node kernel for the plurality of pairs of directed acyclic graphs.

7. The method of claim 6, further comprising determining a success or failure of the fusion using a sigmoid layer.

8. The method of claim 1, wherein the patient is a non-human animal.

9. The method of claim 1, wherein the drug to be prescribed is to treat covid-19.

10. The method of claim 1, wherein the demographic information of the patient comprises a gender of the patient and an age of the patient.

11. A system for computing a probable drug efficacy comprising a processor, memory accessible by the processor and storing computer program instructions and data, and computer program instructions to perform:
for a plurality of patients, generating and storing in the memory a directed acyclic graph representing health events of each patient, each directed acyclic graph comprising:
a first node representing demographic information of the patient,
a plurality of additional nodes, each additional node representing a medical event of the patient,
at least one first edge connecting the first node to an additional node, and
a plurality of additional edges, each additional edge connecting nodes representing two consecutive medical events, the edge having a weight based on a time difference between the two consecutive medical events;
capturing, using the processor, a plurality of features from each directed acyclic graph stored in the memory;
training a classifier model using a plurality of the captured features of each directed acyclic graph;
applying the classifier model to determine a probability that a drug or treatment will be effective for a particular patient; and
determining, using the processor, a drug or treatment to be prescribed to the particular patient based on the determined probability.

12. The system of claim 11, wherein the classifier model comprises a deep learning model.

13. The system of claim 12, wherein the deep learning model comprises a neural network.

14. The system of claim 11, The method of claim 1, wherein the plurality of features are captured by:
transforming each directed acyclic graph to a shortest path graph;
generating a temporal topological kernel by recursively calculating similarity among temporal ordering on a plurality of groups of additional nodes; and
generating a temporal substructure kernel on additional edges connecting additional nodes in each group of additional nodes.

15. The system of claim 11, wherein the plurality of features are captured by:
generating a topological ordering of each directed acyclic graph based on an order of occurrence of a label associated with each additional node in each directed acyclic graph;
generating a topological sequence of each directed acyclic graph comprising a plurality of levels indicating an order of occurrence of a same node label in the topological sequence;
generating a temporal signature for each directed acyclic graph comprising a series of total passage times from the first node to each additional node in a union of a plurality of topological sequences;
generating a temporal proximity kernel between a plurality of pairs of temporal signatures;
generating a shortest path kernel by calculating an edge walk similarity on shortest path graphs for a plurality of pairs of directed acyclic graphs;
generating a node kernel by comparing node labels of a plurality of pairs of directed acyclic graphs; and
fusing the temporal proximity kernel, the shortest path kernel, and the node kernel.

16. The system of claim 15, wherein the fusing comprises:
reducing dimensions of the temporal proximity kernel, the shortest path kernel, and the node kernel for the plurality of pairs of directed acyclic graphs; and
averaging embeddings of the temporal proximity kernel, the shortest path kernel, and the node kernel for the plurality of pairs of directed acyclic graphs.

17. The system of claim 16, further comprising determining a success or failure of the fusion using a sigmoid layer.

18. The system of claim 11, wherein the patient is a non-human animal.

19. The system of claim 11, wherein the drug to be prescribed is to treat covid-19.

20. The system of claim 11, wherein the demographic information of the patient comprises a gender of the patient and an age of the patient.

21. A computer program product for computing a probable drug efficacy, the computer program product comprising a non-transitory computer readable storage having program instructions embodied therewith, the program instructions executable by a computer, to cause the computer to perform a method comprising:
for a plurality of patients, generating and storing in the memory a directed acyclic graph representing health events of each patient, each directed acyclic graph comprising:
a first node representing demographic information of the patient,
a plurality of additional nodes, each additional node representing a medical event of the patient,
at least one first edge connecting the first node to an additional node, and
a plurality of additional edges, each additional edge connecting nodes representing two consecutive medical events, the edge having a weight based on a time difference between the two consecutive medical events;

capturing, using the processor, a plurality of features from each directed acyclic graph stored in the memory;

training a classifier model using a plurality of the captured features of each directed acyclic graph;

applying the classifier model to determine a probability that a drug or treatment will be effective for a particular patient; and determining, using the processor, a drug or treatment to be prescribed to the particular patient based on the determined probability.

22. The computer program product of claim 21, wherein the classifier model comprises a deep learning model.

23. The computer program product of claim 22, wherein the deep learning model comprises a neural network.

24. The computer program product of claim 21, The method of claim 1, wherein the plurality of features are captured by:

transforming each directed acyclic graph to a shortest path graph;

generating a temporal topological kernel by recursively calculating similarity among temporal ordering on a plurality of groups of additional nodes; and generating a temporal substructure kernel on additional edges connecting additional nodes in each group of additional nodes.

25. The computer program product of claim 21, wherein the plurality of features are captured by:

generating a topological ordering of each directed acyclic graph based on an order of occurrence of a label associated with each additional node in each directed acyclic graph;

generating a topological sequence of each directed acyclic graph comprising a plurality of levels indicating an order of occurrence of a same node label in the topological sequence;

generating a temporal signature for each directed acyclic graph comprising a series of total passage times from the first node to each additional node in a union of a plurality of topological sequences;

generating a temporal proximity kernel between a plurality of pairs of temporal signatures;

generating a shortest path kernel by calculating an edge walk similarity on shortest path graphs for a plurality of pairs of directed acyclic graphs;

generating a node kernel by comparing node labels of a plurality of pairs of directed acyclic graphs; and fusing the temporal proximity kernel, the shortest path kernel, and the node kernel.

26. The computer program product of claim 25, wherein the fusing comprises:

reducing dimensions of the temporal proximity kernel, the shortest path kernel, and the node kernel for the plurality of pairs of directed acyclic graphs; and averaging embeddings of the temporal proximity kernel, the shortest path kernel, and the node kernel for the plurality of pairs of directed acyclic graphs.

27. The computer program product of claim 26, further comprising determining a success or failure of the fusion using a sigmoid layer.

28. The computer program product of claim 21, wherein the patient is a non-human animal.

29. The computer program product of claim 21, wherein the drug to be prescribed is to treat covid-19.

30. The computer program product of claim 21, wherein the demographic information of the patient comprises a gender of the patient and an age of the patient.

* * * * *